US011135278B2

(12) United States Patent
Rhee et al.

(10) Patent No.: US 11,135,278 B2
(45) Date of Patent: Oct. 5, 2021

(54) PHARMACEUTICAL COMPOSITION COMPRISING ATTENUATED *STREPTOCOCCUS PNEUMONIAE* STRAINS AND USE THEREOF

(71) Applicant: DOKNIP BIOPHARM CO., Changwon-si (KR)

(72) Inventors: Dong-Kwon Rhee, Suwon-si (KR); Seung-Han Seon, Suwon-si (KR); Bo-Gyung Kim, Suwon-si (KR)

(73) Assignee: DOKNIP BIOPHARM CO., Changwon-si (KR)

( * ) Notice: Subject to any disclaimer, the term of this patent is extended or adjusted under 35 U.S.C. 154(b) by 0 days.

(21) Appl. No.: 16/608,967

(22) PCT Filed: Apr. 25, 2018

(86) PCT No.: PCT/KR2018/004800
§ 371 (c)(1),
(2) Date: Oct. 28, 2019

(87) PCT Pub. No.: WO2018/199628
PCT Pub. Date: Nov. 1, 2018

(65) Prior Publication Data
US 2020/0282039 A1 Sep. 10, 2020

(30) Foreign Application Priority Data

Apr. 26, 2017 (KR) .................. 10-2017-0053512
Mar. 14, 2018 (KR) .................. 10-2018-0029765

(51) Int. Cl.
*A61K 35/74* (2015.01)
*A61K 39/39* (2006.01)
*A61K 39/09* (2006.01)
*A61P 11/06* (2006.01)
*A61P 37/08* (2006.01)
*A61P 31/04* (2006.01)
*A61P 1/00* (2006.01)
*A61P 31/16* (2006.01)
*A61K 39/00* (2006.01)

(52) U.S. Cl.
CPC ............ *A61K 39/092* (2013.01); *A61K 35/74* (2013.01); *A61K 39/39* (2013.01); *A61P 1/00* (2018.01); *A61P 11/06* (2018.01); *A61P 31/04* (2018.01); *A61P 31/16* (2018.01); *A61P 37/08* (2018.01); *A61K 2039/522* (2013.01); *A61K 2039/542* (2013.01); *A61K 2039/543* (2013.01); *A61K 2039/57* (2013.01)

(58) Field of Classification Search
None
See application file for complete search history.

(56) References Cited

U.S. PATENT DOCUMENTS 8,226,959 B2 7/2012 Gibson et al.

FOREIGN PATENT DOCUMENTS

| KR | 10-2006-0108703 A | 10/2006 |
|---|---|---|
| KR | 10-0814616 B1 | 3/2008 |
| KR | 10-2012-0010906 A | 2/2012 |
| KR | 10-1252911 B1 | 4/2013 |
| KR | 20120010906 * | 4/2013 |
| WO | 2010035954 A2 | 4/2010 |

OTHER PUBLICATIONS

Gina Program "Global Strategy for Asthma Management and Prevention" Global Initiative for Asthma 2016, p. 151.
Ruchi S. Gupta et al. "The 2007 National Asthma Education and Prevention Program Asthma Guidelines: Accelerating Their Implementation and Facilitating Their Impact on Children With Asthma" Mar. 3 2009, vol. 123, Pediatrics, Chicago, Illinois.
Ruth Maron et al, "Mucosal Administration of Heat Shock Protein-65 Decreases Atherosclerosis and Inflammation in Aortic Arch of Low-Density Lipoprotein Receptor-Deficient Mice", American Heart Association, Inc., Jun. 25 2002, p. 1708-1715, vol. 106 Issue 13, American Heart Association, Boston, MA.
Howard L. Weiner, "Oral tolerance: immune mechanisms and the generation of Th3-type TGF-beta-secreting regulatory cells", Microbes and Infection, Sep. 2001, p. 947-954, vol. 3 Issue 11, Elsevier, Boston, MA.
Donghyun Kim et al, "Nod2-mediated recognition of the microbiota is critical for mucosal adjuvant activity of cholera toxin", Nature Medicine, May 2016, p. 524-530, vol. 22 Issue 5, Nature Publishing Group, United States of America.
Mats Kalin, "Pneumococcal serotypes and their clinical relevance", Thorax, Mar. 1, 1998, p. 159-162, vol. 53 Issue 3, BMJ Group, United Kingdom.
C. Anandan et al, "Is the prevalence of asthma declining? Systematic review of epidemiological studies", Allergy, Jan. 5, 2010, p. 152-16, vol. 65 Issue 2, John Wiley & Sons, Inc., United Kingdom.
Bengt Bjorksten, "Primary prevention of atopic asthma", Current Opinion in Allergy and Clinical Immunology, Dec. 2001, p. 545-548, vol. 1 Issue 6, Lippincott Williams & Wilkins, Stockholm, Sweden.
Marko Kalliomaki et al, "Probiotics in primary prevention of atopic disease: a randomised placebo-controlled trial", The Lancet, Apr. 7, 2001, p. 1076-1079, vol. 357 Issue 9262, Turku, Finland.
John Penders et al, "The role of the intestinal microbiota in the development of atopic disorders", Allergy, May 10, 2007, p. 1223-1236, vol. 62 Issue 11, John Wiley & Sons, Inc., Maastricht, The Netherlands.
Markus Hilty et al, "Disordered Microbial Communities in Asthmatic Airways", PLOS One, Jan. 5, 2010, p. 1-9, vol. 5 Issue 1, Public Library of Science (PLOS), UK.

(Continued)

*Primary Examiner* — Padmavathi Baskar
(74) *Attorney, Agent, or Firm* — Novick, Kim & Lee, PLLC; Sang Ho Lee; Hyun Woo Shin

(57) ABSTRACT

Provided is a pharmaceutical composition including attenuated *Streptococcus pneumoniae* strains, and a method thereof for prevention or treatment of inflammatory diseases, respiratory viral infections, bacterial infectious diseases, or allergic diseases.

12 Claims, 20 Drawing Sheets

Specification includes a Sequence Listing.

(56) References Cited

OTHER PUBLICATIONS

Benjamin J. Green et al, "Potentially Pathogenic Airway Bacteria and Neutrophilic Inflammation in Treatment Resistant Severe Asthma", PLOS One, Jun. 2014, p. 1-7, vol. 9 Issue 6, Public Library of Science (PLOS), UK.

Ayse Bilge Ozturk et al, "The Potential for Emerging Microbiome-Mediated Therapeutics in Asthma", Current Allergy and Asthma Reports, Aug. 10, 2017, p. 1-12, vol. 17 Issue 62, Springer US, United States of America.

Samy Suissa et al, "Low-dose inhaled corticosteroids and the prevention of death from asthma.", New England Journal of Medicine, Aug. 3, 2000, p. 332-336, vol. 343 Issue 5, Massachusetts Medical Society, United States of America.

A. Durham et al, "Steroid resistance in severe asthma: current mechanisms and future treatment.", Current Pharmaceutical Design, 2011, p. 674-684, vol. 17 Issue 7, Bentham Science Publishers, United States of America.

R. Novak et al, "Emergence of vancomycin tolerance in *Streptococcus pneumoniae*", Nature, Jun. 10, 1999, p. 590-593, vol. 399 Issue 6736, Nature Publishing Group, United States of America.

Oswald T. Avery et al, "Studies on the Chemical Nature of the Substance Inducing Transformation of Pneumococcal Types", Journal of Experimental Medicine, Nov. 1, 1943, p. 137-159, vol. 79 Issue 2, Rockefeller University Press, United States of America.

Larry S. McDaniel et al, "Monoclonal Antibodies Against Proteasesensitive Pneumococcal Antigens Can Protect Mice From Fatal Infection With *Streptococcus pneumoniae*", Journal of Experimental Medicine, Aug. 1, 1984, p. 386-397, vol. 160 Issue 2, Rockefeller University Press, United States of America.

Ingeborg S. Aaberge et al, "Virulence of *Streptococcus pneumoniae* in mice: a standardized method for preparation and frozen storage of the experimental bacterial inoculum", Microbial Pathogenesis, Jan. 27, 1995, p. 141-152, vol. 18 Issue 2, Oslo, Norway.

David E Briles et al, "Mouse Antibody to Phosphocholine Can Protect Mice from Infection with Mouse-Virulent Human Isolates of *Streptococcus pneumoniae*", Infection and Immunity, May 1992, p. 1957-1962, vol. 60 Issue 5, American Society for Microbiology, United States of America.

Sang-Yoon Choi et al, "Inactivated pep27 mutant as an effective mucosal vaccine against a secondary lethal pneumococcal challenge in mice", Clinical and Experimental Vaccine Reasearch, Jan. 2013, p. 58-65, vol. 2 Issue 1, Korean Vaccine Society, Republic of Korea.

Eun-Hye Kim et al, "*Streptococcus pneumoniae* pep27 mutant as a live vaccine for serotype-independent protection in mice", Vaccine, Mar. 2, 2012, p. 2008-2019, vol. 30 Issue 11, South Korea.

Byoung-Shik Shim et al, "Sublingual Administration of Bacteria-Expressed Influenza Virus Hemagglutinin 1 (HA1) Induces Protection against Infection with 2009 Pandemic H1N1 Influenza Virus", Journal of Microbiology, 2013, p. 130-135, vol. 51 Issue 1,The Microbiological Society of Korea, Republic of Korea.

Keenan T. Bashour et al, "CD28 and CD3 have complementary roles in T-cell traction forces", Proceedings of the National Academy of Sciences of the United States of America (PNAS), Feb. 11, 2014, p. 2241-2246, vol. 111 Issue 6, National Academy of Sciences, United States of America.

Jonathan M. Cohen et al, "Lack of cross-protection against invasive pneumonia caused by heterologous strains following murine *Streptococcus pneumoniae* nasopharyngeal colonisation despite whole cell ELISAs showing significant cross-reactive IgG", Vaccine, May 1, 2013, p. 2328-2332, vol. 31 Issue 19, UK.

Aoife M. Roche et al, "Live Attenuated Streptococcus pneumoniae Strains Induce Serotype-Independent Mucosal and Systemic Protection in Mice", Infection and Immunity, May 2007, p. 2469-2475, vol. 75 Issue 5, American Society for Microbiology, United States of America.

Yuet Wu et al, "Lethal coinfection of influenza virus and Streptococcus pneumoniae lowers antibody response to influenza virus in lung and reduces numbers of germinal center B cells, T follicular helper cells, and plasma cells in mediastinal lymph Node", Journal of Virology, Feb. 2015, p. 2013-2023, vol. 89 Issue 4, American Society for Microbiology, Hong Kong, China.

Stefan Wirtz et al, "Chemically induced mouse models of intestinal inflammation", Nature Protocols, Mar. 15, 2007, p. 541-546, vol. 2 Issue 3, University of Mainz, Mainz, Germany.

Samir Jawhara et al, "*Saccharomyces boulardii* decreases inflammation and intestinal colonization by Candida albicans in a mouse model of chemically-induced colitis", Medical Mycology, Dec. 1, 2007, p. 691-700, vol. 45 Issue 8, Oxford University Press, France.

Yinghua Xu et al, "The correlation between proinflammatory cytokines, MAdCAM-1 and cellular infiltration in the inflamed colon from TNF-a gene knockout mice", Immunology and Cell Biology, Sep. 4, 2007, p. 633-639, vol. 85 Issue 8, John Wiley and Sons, Inc., Australia.

Astrid A.T.M. Bosch et al, "Viral and Bacterial Interactions in the Upper Respiratory Tract", PLOS Pathogens, Jan. 2013, p. 1-12, vol. 9 Issue 1, University Medical Center-Wilhelmina Children's Hospital,, The Netherlands.

Joshua R. Shak et al, "Influence of bacterial interactions on pneumococcal colonization of the nasopharynx", Trends in Microbiology, Mar. 2013, p. 129-135, vol. 21 Issue 3, United States of America.

Michael J. Mina et al, "Pathogen Replication, Host Inflammation, and Disease in the Upper Respiratory Tract", Infection and Immunity, Mar. 2013, p. 625-628, vol. 81 Issue 3, Emory University, Atlanta, Georgia, United States of America.

Dennis W. Metzger et al, "Limited Efficacy of Antibacterial Vaccination Against Secondary Serotype 3 Pneumococcal Pneumonia Following Influenza Infection", Journal of Infectious Diseases, Aug. 1, 2015, p. 445-452, vol. 212 Issue 3, Center for Immunology and Microbial Disease, Albany Medical College, New York.

Fiona Pigny et al, "Intranasal Vaccination With *Salmonella*-Derived Serodominant Secreted Effector Protein B Associated With Gas-Filled Microbubbles Partially Protects Against Gut Infection in Mice", Journal of Infectious Diseases, Aug. 1, 2016, p. 438-446, vol. 214 Issue 3, Switzerland.

S.H. Cho et al, "Peripheral blood CD4+ and CD8+ T cell type 1 and type 2 cytokine production in atopic asthmatic and normal subjects", Clinical & Experimental Allergy, 2002, p. 427-433, vol. 32 Issue 3, London UK.

Ming et al, "Effect of inhaled inactivated *Mycobacterium phlei* in children with moderate asthma", Immunotherapy, Feb. 2013, p. 191-197, vol. 5 Issue 2, The First Affiliated Hospital of Guangxi, Guangxi, China.

Ming et al, "The effect of inhaled inactived *Mycobacterium phlei* as a treatment for asthma", Molecular Medicine Reports, Feb. 2017, p. 777-783, vol. 15 Issue 2, Spandidos Publications, Guangxi, P.R. China.

R. Li et al, "Attenuated Bordetella pertussis BPZE1 protects against allergic airway inflammation and contact dermatitis in mouse models", Allergy, 2012, p. 1250-1258, vol. 67 Issue 10, Shanghai, China.

C. Gruber et al, "Common vaccine antigens inhibit allergen-induced sensitization and airway hyperresponsiveness in a murine model", Allergy, Jul. 2006, p. 820-827, vol. 61 Issue 7, Pediatric Pneumology and Immunology, Charite—Universitatsmedizin Berlin, Germany.

J.A. Preston et al, "*Streptococcus pneumoniae* infection suppresses allergic airways disease by inducing regulatory T-cells", European Respiratory Journal, Jan. 2011, p. 53-64, vol. 37 Issue 1, European Respiratory Society, Australia.

Alison N. Thorburn et al, "Pneumococcal conjugate vaccine-induced regulatory T cells suppress the development of allergic airways disease", Thorax, Dec. 2010, p. 1053-1060, vol. 65 Issue 12, BMJ Group, Australia.

Alison N. Thorburn et al, "Pneumococcal Components Induce Regulatory T Cells That Attenuate the Development of Allergic Airways Disease by Deviating and Suppressing the Immune Response to Allergen", Journal of mmunology, Oct. 15, 2013, p. 4112-4020, vol. 191 Issue 8, American Association of Immunologists, United States of America.

Kenji Takabayashi et al, "Intranasal Immunotherapy Is More Effective Than Intradermal Immunotherapy for the Induction of Airway Allergen Tolerance in Th2-Sensitized Mice", Journal of Immunol-

(56) References Cited

OTHER PUBLICATIONS ogy, Apr. 1, 2003, p. 3898-3905, vol. 170 Issue 7, American Association of Immunologists, United States of America.

D.P. Ennis et al, "Prior Bordetella pertussis infection modulates allergen priming and the severity of airway pathology in a murine model of allergic asthma", Clinical & Experimental Allergy, Sep. 2004, p. 1488-1497, vol. 34 Issue 9, Dublin, Ireland.

Rakesh K. Kumar et al, "Effects of Anticytokine Therapy in a Mouse Model of Chronic Asthma", American Journal of Respiratory and Critical Care Medicine, Nov. 15, 2004, p. 1043-1048, vol. 170 Issue 10, American Thoracic Society, Malvern, Pennsylvania.

Julie A. Preston et al, "Inhibition of allergic airways disease by immunomodulatory therapy with whole killed *Streptococcus pneumoniae*", Vaccine, Nov. 25, 2007, p. 8154-8162, vol. 25 Issue 48, Australia.

Gyu-Lee Kim et al, "Pneumococcal pep27 mutant immunization stimulates cytokine secretion and confers long-term immunity with a wide range of protection, including against non-typeable strains", Vaccine, Nov. 12, 2016, p. 6481-6492, vol. 34 Issue 51, United States of America.

Jason W. Rosch et al, "A live-attenuated pneumococcal vaccine elicits CD4+ T-cell dependent class switching and provides serotype independent protection against acute otitis media", EMBO Molecular Medicine, Nov. 2013, p. 141-154, vol. 6 Issue 1, United States of America.

Ana M.C. Faria et al., "Oral tolerance" Immunological Reviews 2005, vol. 206, p. 232-259, United States of America.

Knudson, C. J et al., "The Relationship Between Respiratory Syncytial Virus and Asthma", Veterinary Pathology, 2015, vol. 52, No. 1, pp. 97-106.

WHO "Global surveillance, prevention and control of chronic respiratory diseases" A comprehensive approach 2007, p. 155.

Seung Han Seon et al., "Intranasal Immunization With an Attenuated pep27 Mutant Provides Protection From Influenza Virus and Secondary Pneumococcal Infections", The Journal of Infectious Disease, 2017, 217: 637-640.

Prachetash Ghosh et al., "Pneumococcal VncR Strain-Specifically Regulates Capsule Polysaccharide Synthesis", vol. 10, Oct. 2019.

\* cited by examiner

Assay of ΔPep27 Immunization for Inhibition against DSS-Induced Enterocolitis in Mice

PHARMACEUTICAL COMPOSITION COMPRISING ATTENUATED *STREPTOCOCCUS PNEUMONIAE* STRAINS AND USE THEREOF

INCORPORATION OF SEQUENCE LISTING

This application contains a sequence listing submitted in Computer Readable Form (CRF). The CFR file containing the sequence listing is entitled "13-PL5183460-Sequence-Listing.txt", which was created and modified on Oct. 28, 2019, and is 3,884 bytes in size. The information in the sequence listing is incorporated herein by reference in its entirety.

TECHNICAL FIELD

The disclosure pertains to a pharmaceutical composition comprising an attenuated *Streptococcus pneumoniae* strain and a use thereof in preventing or treating inflammatory diseases, respiratory viral infections, or bacterial infectious diseases.

In addition, the disclosure pertains to a pharmaceutical composition comprising an attenuated *Streptococcus pneumoniae* strain and a use thereof in preventing or treating allergic diseases.

BACKGROUND ART

According to reports, intranasal or oral administration of antigens induced regulatory T (Treg) cells which, in turn, induce mucosal tolerance in target organs (Faria and Weiner, 2005). Also reportedly (Faria and Weiner, 2005), the induction of mucosal tolerance suppressed various autoimmune diseases including atherosclerosis in mice (Maron et al, 2002). Accordingly, the principle of mucosal tolerance may be applied to animals and humans. Multiple mucosal stimulations by antigen administration induces T cells to secrete anti-inflammatory cytokines such as IL-10 or TGF-$\beta$1 to protect the tissues and induce mucosal tolerance (Faria and Weiner, 2005; Weiner, 2001). In order to maintain immune tolerance on the mucosal surface, a certain type of Treg cells are preferentially induced, but the induction mechanism thereof remains uncertain.

Meanwhile, currently used mucosal vaccines are too weak in potency to induce sufficient immune responses without adjuvants. Mucosal adjuvants are used for antigens that induce low immune tolerance when administered alone. Cholera toxin B subunit (CTB) may be exemplified as a mucosal adjuvant (Faria and Weiner, 2005). However, the immunity enhancement effect of cholera toxin after intranasal inoculation accounts for the bacterial recognition and mediation (Kim et al, 2016) and thus the essential role of microorganisms in the potentiation, implying that it is preferred that attenuated bacteria may be used as an adjuvant as needed. That is to say, the concept of adjuvant-free mucosal vaccines has not yet been proven, thus far.

Furthermore, nowhere has it been reported in previous documents whether mucosal vaccines can also exhibit an effect on various other diseases in addition to diseases directly related to the antigens used in the vaccines. Currently available immunotherapy protects against only the antigens used in vaccination. Specifically, for prevention of pneumococcal disease, 23-valent polysaccharide vaccines or 13-valent conjugate vaccines are used. However, 23-valent polysaccharide vaccine cannot induce the production of immunological memory cells and 13-valent conjugate vaccine can protect against only 13 serotypes among 90 or more serotypes (Kalin, 1998).

Asthma is one of the most common chronic diseases in both children and adults in the world (Anandan et al., 2010). As many as about 300 million people worldwide are affected by asthma, costing extensive medical expenses (WHO, 2007). Global numbers of asthma patients are predicted to increase each year, with an additional 100 million people suffering from the disease by 2025. According to statistics from the US Centers for Disease Control and Prevention, asthma patients amounted to 3.1% of the population in the United States in 1980 and increased up to 8.4% in 2010, with an increase tendency ongoing (https://www.cdc.gov/asthma). In addition, 70% of asthma patients also suffer from allergies [GINA guidelines, 2016]. In 2015, asthma was diagnosed in 1.66 million people of South Korea (2015 statistics of the Health Insurance Review & Assessment Service), ranking sixth in terms of the burden of disease among the top ten chronic diseases in the population of South Korea.

The onset of asthma and other allergic diseases is in close association with environmental changes toward the Western lifestyle and urbanization (GINA guidelines, 2016). Asthma is a heterogeneous disease with various causes, usually caused by inflammation. Asthma patients exhibit similar symptoms, but with underlying mechanisms different from each other (GINA guidelines, 2016; National Asthma Education and Prevention Program, 2007). In addition, modalities of airway inflammation are different from each other, depending on kinds of asthma (GINA guidelines, 2016). A typical pathogenic mechanism of asthma is immunoglobulin E (IgE)-mediated eosinophilic airway inflammation and many results of pathology and asthma studies have focused on Th2-related acquired immune responses (GINA guidelines, 2016). However, recent studies have focused on innate immunity, microbiomes, microbes within the body, and the like (Bjorksten et al., 2001; Kalliomaki et al., 2001; Penders et al., 2007; Hilty et al., 2010; Green et al., 2014; and Ozturk et al., 2017).

According to the Asthma and Allergy Foundation of America (http://www.aafa.org/), currently available asthma-related drugs can reduce symptoms only for asthma management, but cannot cure asthma completely. Asthma is characterized by airway hyper-responsiveness (AHR) that leads to episodes of excessive bronchoconstriction. Even though regular medication with inhaled glucocorticosteroid has significantly reduced mortality over the past years, asthma is still a worldwide cause of about 250,000 deaths in each year, and has a significant burden of disease (Suissa et al., 2000). According to the frequency of symptoms, asthma is classified as mild (1-2 times per month), moderate (1-2 times per week), and severe (asthma symptoms daily). For severe symptoms, daily administration of 3-4 medicines is required. Even a mild symptom needs regular medication. Because asthma is airway inflammation to cause bronchoconstriction, patients with asthma have to spray a bronchodilation inhalant to their throats immediately when undergoing dyspnea. In addition, some of asthma patients and severe asthma patients do not respond to adrenal cortical hormones at all so that they may suffer from the disease throughout their lives or die without experiencing any clinical effects (Durham et al., 2011). The recently marketed anti-IL-5 agents can alleviate asthmatic symptoms by being injected once every four weeks. However, medicines or therapies that can completely cure or prevent asthma have not yet been developed or reported, thus far.

DETAILED DESCRIPTION OF THE INVENTION

Technical Problem

Prophylactic and therapeutic methods for inflammatory diseases attributed to inflammatory factors, such as gut diseases, infection, atherosclerosis, and epithelial lesions, have been developed, but are restricted to the use of certain markers causative of inflammation or diseases. In this regard, because mucosal immunity is expected to prevent mucosal related diseases and inflammatory diseases, the present disclosure suggests a novel anti-inflammatory and protection therapy against various diseases by taking advantage of the mucosal immunity of Pneumococcal whole-cell vaccines. In addition, it is proven in the present disclosure that a vaccine which is administered to mucosa utilizing the immune tolerance of mucosal immunity can be a novel therapy for preventing or treating gut inflammation and infectious diseases.

Furthermore, the present disclosure develops a novel method for protection against a broad spectrum of inflammatory diseases including respiratory viral and bacterial infectious diseases as well as lesions caused by gut inflammation and respiratory infection and inflammation by inoculating a pneumococcal whole-cell vaccine to the mucous membrane.

Moreover, currently available asthma medicines are divided into symptom relieving agents for dilating narrowed airways (bronchodilators) and disease controllers for suppressing airway inflammation to prevent asthmatic attacks (anti-inflammatory agents). The medicines, however, cannot perfectly cure nor prevent asthma. Therefore, the present disclosure provides as a means for preventing or treating allergic diseases including asthma a pharmaceutical composition comprising *Streptococcus pneumoniae* and, particularly, a pharmaceutical composition comprising a *Streptococcus pneumoniae* strain which is attenuated sufficiently to guarantee safety even upon intranasal administration, intraperitoneal injection, and intravenous injection in order to overcome the drawback that the use of *Streptococcus pneumoniae* in pharmaceutical compositions such as vaccines requires inactivating *Streptococcus pneumoniae* or use of separating and purifying particular components of *Streptococcus pneumoniae* due to the high toxicity of the bacteria.

However, the purposes to be achieved in the present disclosure are not limited to the foregoing, and other unmentioned purposes could be understood by those skilled in the art from the following description.

Technical Solution

The present disclosure provides a pharmaceutical composition for preventing or treating inflammatory disease, respiratory viral infectious disease, or infectious diseases of bacteria other than *Streptococcus pneumoniae*, which comprises an attenuated *Streptococcus pneumoniae* strain.

In addition, the present disclosure provides a use of a *Streptococcus pneumoniae* strain attenuated by mutation of pep27 gene in preventing or treating various allergic diseases including allergic respiratory disease, and a pharmaceutical composition used therefor.

The solutions set forth above are only illustrative and should not be construed to limit the present invention. In addition to the above-described exemplary embodiments, there may be additional embodiments and examples that are explained in the drawings and the description.

Advantageous Effects

According to the present disclosure, mucosal inoculation by the pneumococcal whole-cell vaccine induces the expression of immunization related to genes in the lung and the spleen, thereby preventing and/or treating inflammation-related diseases.

Particularly, while conventional vaccines may provide protection against only specific antigenic ingredients, the use of the pneumococcal mucosal vaccine according to the present disclosure is expected to exhibit a broad range of prophylactic and therapeutic effects including protecting potentials against inflammatory diseases of other organ as well as viral and bacterial infectious diseases. In addition, when administered to the mucosal membrane, the pneumococcal whole-cell vaccine according to the present disclosure can provide protective effects against a variety of diseases even without any adjuvant, in contrast to conventional mucosal vaccines.

The present disclosure also provides a method for preventing or treating allergic diseases including asthma by using a *Streptococcus pneumoniae* pep27 mutant. Particularly, vaccination with the *Streptococcus pneumoniae* pep27 mutant can lead to prevention or treatment of allergic respiratory diseases including asthma, allergic rhinitis, sinusitis, and chronic obstructive pulmonary disease and other allergic diseases including hives, conjunctivitis, pollen allergy, and atopy.

Furthermore, the *Streptococcus pneumoniae* pep27 mutant according to the present disclosure has the advantage of guaranteeing safety even upon intranasal administration, intraperitoneal injection, and intravenous injection because the mutant is sufficiently attenuated.

BRIEF DESCRIPTION OF THE DRAWINGS

In FIG. 1, the genes of the immunized lung tissue are shown to suppress gastroenteritis and abnormality of the large intestine while FIG. 2 depicts the protective effect of the gene of the spleen on influenza virus infection.

In FIG. 4, mice (n=3) were intranasally immunized with Δpep27 every two weeks for a total of three times, and on day 7 after the last immunization, spleen cells were isolated and labeled with fluorescence cell makers against Th1 (CD4, Tbet), Th2 (CD4, GATA3), Th17 (CD4, RORγt), and Treg (CD4, Foxp3) and then detected by flow cytometry.

FIGS. 5 and 6 show levels of cytokines in splenocytes (FIG. 5) and sera (FIG. 6) obtained on day 7 after the last immunization, as measured by ELISA. Statistical significance was analyzed by ANOVA; *, P<0.05, **, P<0.01.

BEST MODE FOR CARRYING OUT THE INVENTION

Figure 1:
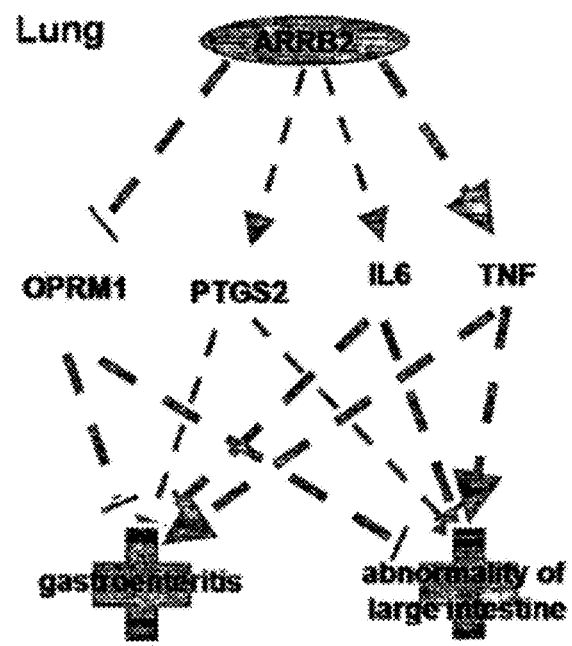
FIGS. 1 and 2 are schematic diagrams showing analysis results of the *Streptococcus pneumoniae* vaccine functions in the lung (FIG. 1) and the spleen (FIG. 2) as measured by system biology analysis in accordance with one embodiment of the present disclosure. Mice were immunized with THpep27 mutant (Δpep27) every two weeks for a total of three times. Two weeks after the last immunization, lungs and spleens were excised and total RNA was extracted therefrom. Gene expression was determined by high-throughput sequencing, followed by analysis using Ingenuity Pathway Analysis.

Exemplary embodiments of the present invention will be described more fully with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, elements irrelevant to the description will be omitted for clarity.

Throughout the specification, unless explicitly described to the contrary, the word "comprise" and variations such as "comprises" or "comprising" will be understood to imply the inclusion of stated elements but not the exclusion of any other elements.

Words of degree, such as "about", "substantially", and the like are used in the present specification in the sense of "at, or nearly at, when given the manufacturing, design, and material tolerances inherent in the stated circumstances" and are used to prevent the unscrupulous infringer from unfairly taking advantage of the invention disclosure where exact or absolute figures are stated as an aid to understanding the invention. The terms "a step of", which are used throughout the description, does not mean "a step for".

Throughout the description, the term "combination of" included in Markush type description means mixture or combination of one or more components, steps, operations and/or elements selected from a group consisting of components, steps, operation and/or elements described in Markush type and thereby means that the present invention includes one or more components, steps, operations and/or elements selected from the Markush group.

Throughout the description, the expression "A and/or B" means "A, B, or A and B".

Throughout the description, "*Streptococcus pneumoniae*", also called pneumococcus, is a Gram-positive bacterium of the genus *Streptococcus* and it is classified to the family of *Streptococcus* because the bacteria appear to form chains as cell division therein occurs along a single axis over time. The bacterium is known as a leading cause of pneumonia.

Throughout the description, "Pep27", which is composed of 27 amino acid residues, is secreted by a vex transporter system to induce growth inhibition and apoptosis. In detail, expression of pep27 induces the programmed cell death in *S. pneumoniae* through the signal transduction triggered via the membrane-bound histidine protein kinase vncS and the response regulator vncR, which is a cytoplasmic effector (Novak et al., 1999). Pep27 genes or proteins encoded thereby may be designated differently from one serotype of *Streptococcus pneumoniae* to another and there may be a slight difference in the nucleotide sequence or peptide sequence of pep27. However, so long as it performs substantially the same function as is described above, any pep27 gene may be mutated and used irrespective of serotypes to prepare the attenuated *Streptococcus pneumoniae* strain of the present invention. Particularly, any gene of *Streptococcus pneumoniae* that is functionally the same as the pep27 gene may be employed in the present disclosure. More particularly, the pep27 gene of the present disclosure may be damaged by mutation of a gene coding for the pep27 peptide sequence represented by SEQ ID NO: 1.

As used herein, the term "attenuation" is intended to refer to modification of a virulent strain into a less virulent strain or a weaker pathogen before modification. This attenuated strain refers to a strain which is significantly reduced in virulence related to clinical diseases while still replicating within a host. Particularly, the attenuated strain of the present disclosure is of such a low virulence or pathogenicity so as to allow itself to be administered as a vaccine. More particularly, the pneumococcal strains of the present invention are attenuated to the extent that they cannot cause clinical diseases while remaining replicable within hosts. The attenuated mutant can be obtained using a variety of different methods, such as point mutation, sequence exchange between related viruses, or nucleotide deletion.

Throughout the description as used herein, the term "mutation" is intended to mean all actions causing an alteration in the genetic function of a gene. In detail, "mutation" refers to the quantitative or qualitative change in a gene among various biological variations.

Throughout the description the term "allergy", as used herein, refers to a number of disorders, diseases, or abnormal conditions caused by hypersensitivity of the immune system to certain substances, that is, an excessive reaction of the immune system to foreign substances. Allergic diseases to which the composition of the present disclosure is applied are those resulting particularly from type I immediate hypersensitivity and type IV delayed hypersensitivity. Examples of type I immediate hypersensitivity include bronchial asthma, rhinitis, atopic dermatitis, conjunctivitis, tympanitis, hives, and anaphylactic shock. Contact hypersensitivity, contact dermatitis, bacterial allergy, fungal allergy, viral allergy, drug allergy, thyroiditis, and allergic encephalitis fall within the scope of type IV delayed hypersensitivity. Type I immediate hypersensitivity is divided into two stages: In stage 1, exposure to an allergen tips the balance between a Th1 response, which is characterized by the production of IL12 and IFN-γ, which downregulate the secretion of IgE and IgG1 and increase the secretion of IgG2a and a Th2 response, which leads to the production of IL-4, IL-5, and IL-13, in Th2 bias, so that IL-4 and IL-13 produced in response to a Th2-dominated immune response induce B cells to produce allergen-specific IgE which, in turn, binds to the surface of mast cells and basophils, thereby preparing for allergy development. Mast cells and basophils coated by IgE are, so called, sensitized to an allergen; the stage 2 of allergy development is classified into an early response and a late response. In the early response, the mast cells activated upon re-exposure to an allergen undergo degranulation, during which the cells release histamine, lipid metabolites, cytokines, etc. from their granules, causing vasodilation, etc. In the late response, neutrophils, eosinophils, macrophages, Th2 cells, basophils, etc. infiltrate into the corresponding tissues to provoke inflammation, causing atopic dermatitis, rhinitis, asthma, and the like.

Throughout the description as used herein, the term "prevention" means all actions that inhibit or delay the onset of a disease by administration of a composition according to the present disclosure.

Throughout the description as used herein, the term "treatment" or "treating" means all actions that are intended to ameliorate or beneficially change a symptom associated with the disease by administering a composition according to the present disclosure.

Throughout the description as used herein, the term "vaccine" refers to a biological preparation comprising an antigenic substance that resembles a disease-causing microorganism or virus so as to provide active acquired immunity for prevention of the disease caused thereby. A vaccine is often made from attenuated or killed bacterium or virus. The administration of vaccines is called vaccination, which is intended to artificially acquire immunogenicity against particular infection. When stimulated by the vaccine, the immune system in the subject is activated to generate antibodies. The sensitization is maintained, and when reinfection occurs, the antibodies may be effectively generated within a short time, thereby overcoming the disease. Meanwhile, thanks to the immune tolerance principle thereof, the vaccine comprising attenuated *Streptococcus pneumoniae* according to the present disclosure can not only protect against particular antigenic substance, but also exhibit prophylactic and therapeutic effects against a broad spectrum of diseases including viral and bacterial infectious diseases, in contrast to conventional vaccines.

The term "ermB", as used herein, means a gene that allows resistance to macrolides. Macrolides are a class of substitutes to penicillin in the therapy of diseases caused by *Streptococcus pneumoniae* and include erythromycin, clarithromycin, and azithromycin.

Hereafter, a detailed description will be given of the pharmaceutical composition comprising an attenuated *Streptococcus pneumoniae* strain according to the present disclosure and a method thereof in preventing or treating inflammatory diseases and respiratory viral or bacterial infectious disease with reference to exemplary embodiments and the drawings. However, the present disclosure should not be understood to be limited to the exemplary embodiments and drawings.

A first aspect of the present disclosure provides a pharmaceutical composition for prevention or treatment of inflammatory diseases, respiratory viral infectious diseases, infectious diseases caused by bacteria other than *Streptococcus pneumoniae*, the composition comprising an attenuated *Streptococcus pneumoniae* strain. For example, the pharmaceutical composition may include a vaccine composition.

According to one embodiment of the present disclosure, the attenuated *Streptococcus pneumoniae* strain may be one in which a part or the entirety of the pep27 gene is deleted. For example, nucleotide residues of positions 1 to 53 on the pep27 nucleotide sequence represented by SEQ ID NO: 1 may be deleted, but there is not limited thereto.

According to another embodiment of the present disclosure, the attenuated *Streptococcus pneumoniae* strain may comprise a mutant pep27 gene in which the nucleotide residues of positions 1 to 53 on the pep27 nucleotide sequence represented by SEQ ID NO: 1 are deleted and substituted with an ermB cassette, but the present disclosure is not limited thereby. By way of example, the attenuated *Streptococcus pneumoniae* strain may be the attenuated *Streptococcus pneumoniae* strain comprising a mutated pep27 gene, disclosed in Korean Patent No. 10-1252911.

According to yet another embodiment of the present disclosure, the inflammatory diseases may be selected from the group consisting of asthma, bronchitis, rhinitis, inflammatory bowel diseases, gastroenteritis, colitis, Crohn's disease, pancreatitis, atherosclerosis, and arthritis, but are not limited thereto. For example, the prevention or treatment of inflammatory diseases may be the effect resulting from downregulating the expression of an inflammation-related gene such as a large intestine inflammation-related gene. The inflammatory diseases may be related to, for example, intestinal and respiratory infectious diseases, but are not limited thereto.

The respiratory infectious diseases may be caused by a respiratory virus that may be selected from, for example, metapneumovirus, coronavirus, enterovirus, respiratory syncytial virus, adenovirus, bocavirus, rhinovirus, and influenza virus. The prevention or treatment of infectious diseases caused by the respiratory virus may be an effect resulting from suppressing the replication of the viruses.

For example, the influenza virus may be influenza A, B, or C and is not limited by concrete subtypes thereof.

In addition, the pharmaceutical composition of the present disclosure may provide a virus non-specific protective function. In this context, the pharmaceutical composition may provide a protective function against influenza viruses and other viruses such as, but not limited to, respiratory syncytial virus and rhinovirus.

According to still another embodiment of the present disclosure, the bacterial infectious diseases may be selected from the diseases caused by infection of Gram-positive bacteria, Gram-negative bacteria, and other infectious bacteria, but are not limited thereto. For example, the prevention or treatment of bacterial infectious diseases may be an effect resulting from suppressing the infection of Gram-positive bacterial and/or Gram-negative bacteria.

According to another embodiment of the present disclosure, the Gram-positive bacteria may be selected from the group consisting of *Staphylococcus* spp., *Streptococcus* spp., *Clostridium tetani*, and *Bacillus anthracis* whereas the Gram-negative bacteria may be selected from *Salmonella* spp. *Shigella, Klepsiella pneumoniae, E. coli*, and *Vibrio cholerae*, but are not limited thereto. For example, the Gram-positive bacteria may be *Staphylococcus aureus*.

According to yet another embodiment of the present disclosure, the pharmaceutical composition may allow for immunization in a serotype-independent manner, but is not limited thereto. As used herein, the pharmaceutical composition that allows for immunization in a serotype-independent manner is intended to refer to a pharmaceutical composition that is designed to produce antibodies irrespective of antigens, but not to produce antibodies specific for particular antigens.

According to still another embodiment of the present disclosure, the allergic disease may be an allergic respiratory disease selected from asthma, allergic rhinitis, sinusitis, and chronic obstructive pulmonary disease, but is not limited thereto.

According to one more embodiment of the present disclosure, examples of the allergic disease include food allergy, allergic tympanitis, anaphylactic shock, contact hypersensitivity, allergic contact dermatitis, bacterial allergy, fungal allergy, viral allergy, drug allergy, and allergic encephalitis in addition to hives, conjunctivitis, pollen allergy, and atopy, but are not limited thereto.

The pharmaceutical composition of the present disclosure can suppress the production of a Th1 cytokine and/or a Th2 cytokine which are both responsible for immune hypersensitivity. Here, the Th1 cytokine may be selected from the group consisting of interferon-gamma (IFN-γ), tumor necrosis factor alpha (TNF-α), and interleukin-12 (IL-12) and the Th2 cytokine may be selected from interleukin-4(IL-4), interleukin-5(IL-5), and interleukin-13(IL-13), with no limitations thereto.

Levels of the Th1 cytokine and/or Th2 cytokine may be measured from body fluid such as bronchoalveolar lavage fluid or serum, with no limitations thereto.

According to yet one more embodiment of the present disclosure, the pharmaceutical composition may be non-invasive to the lung, the spleen, blood, or the brain, with no limitations thereto. As used herein, the term "non-invasive" is intended to mean that the pharmaceutical composition does not invade systemic other regions other than the organs, tissues, and cells to which the pharmaceutical composition is directly administered, or is rapidly eliminated from the systemic regions despite invading the regions, as opposed to "invasive" that pertains to penetration into systemic other regions other than organs, tissue, and cells directly administered the pharmaceutical composition, thus damaging the human body.

As used herein, the term "administration" is intended to refer to the introduction of the composition of the present disclosure to a subject in a certain proper manner. So long as it is delivered to a targeted tissue, any route can be used for administration of the composition of the present disclosure. For example, the administration may be carried out via oral, intraperitoneal, intravenous, intramuscular, subcutaneous, intradermal, intranasal, intrapulmonary, intrarectal, intravesicular, transdermal, and intramucosal routes, but is not limited thereto.

According to still one more embodiment of the present disclosure, the pharmaceutical composition may be administered through an intraperitoneal or intramucosal route, but with no limitations thereto. The position of the mucous membrane to which the pharmaceutical composition is to be administered is not particularly limited. A person skilled in the art may properly select a position from among body sites for mucosal administration.

According to another embodiment of the present disclosure, the pharmaceutical composition may be configured to take a nasopharynx mucosal membrane route for administration, but with no limitations thereto. Vaccination via nasopharynx mucosal membranes may utilize for example, an aerosol or drop administration system, but is not limited thereto.

When the pharmaceutical composition of the present disclosure is used, exhibiting effective immunogenicity in a subject even upon the mucosal administration thereof, the pharmaceutical composition of the present disclosure can eliminate the inconvenience of conventional compositions that should be subcutaneously administered with the aid of a syringe, and is advantageous over conventional compositions in terms of administration to infants, who fear injection with a syringe, but with no limitations thereto. No limitations are imparted to the subject to which the pharmaceutical composition of the present disclosure can be administered. Mammals including humans, rats, mice, poultry, etc. may be the subject, but with no limitations thereto. Also, the vaccine composition of the present invention must be administered in a pharmaceutically effective amount. The pharmaceutically effective amount of the composition of the present disclosure varies depending on the sex, body surface area, and age of the patient, the kind and severity of a disease, the sensitivity to the drug, the route and frequency of administration, excretion rate, the time of administration, treatment duration, target cells, expression levels, and other factors well-known in the pharmaceutical art, which can be easily determined by those skilled in the art.

According to another embodiment of the present disclosure, the pharmaceutical composition may further comprise a pharmaceutically acceptable carrier or an adjuvant, with no limitations thereto.

Examples of the carrier useful in the pharmaceutical composition of the present disclosure include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate, and mineral oil, but are not limited thereto.

Any adjuvant typically used in the art can be used in the present disclosure without limitations. Examples of the adjuvant include a cholera toxin binding unit, aluminum salts, lipid emulsion (MF-59), a synthetic detergent (Tween), microspheres, liposomes, and mucoadhesive polymers, but are not limited thereto. New adjuvant forms, if developed, may also be used.

The pharmaceutical composition according to the present disclosure may be formulated into dosage forms, for example, oral dosage forms such as powders, granules, tablets, capsules, suspensions, emulsions, syrups, aerosols, etc., external applications, suppositories, or sterile injections according to conventional method, but is not limited thereto. In detail, for the formulation, a diluent or excipient such as a filler, an expander, a binder, a humectant, a disintegrant, a surfactant, etc. as used conventionally may be employed, without limitations thereto.

For example, solid agents intended for oral administration of the composition of the present disclosure may be in the form of tablets, pills, powders, granules, capsules, and the like. These solid agents are formulated in combination with at least one excipient, such as starch, calcium carbonate, sucrose, lactose, or gelatin. Besides, a lubricant, such as magnesium stearate, talc and the like in addition to simple excipient, may also be added. Liquid agents intended for oral administration include suspensions, internal use solutions, emulsion, syrups, and the like. In addition to a simple diluent such as water or liquid paraffin as used conventionally, various excipients, such as humectants, sweeteners, aromatics, preservatives, and the like may be comprised in the liquid agents for the oral administration of the composition of the present disclosure, with no limitations thereto.

Parenteral dosage forms of the composition of the present disclosure may include sterile aqueous solutions, non-aqueous solutions, suspensions, emulsions, lyophilized agents, and suppositories. As concerns non-aqueous solutions and suspensions, they are made from propylene glycol, polyethylene glycol, vegetable oils such as olive oil, or injectable esters such as ethyl oleate, with no limitations thereto.

MODE FOR CARRYING OUT THE INVENTION

A better understanding of the present disclosure may be obtained through the following Examples which are set forth to illustrate, but it is not to be construed as limiting the present disclosure.

[Example 1] Assay of Inhibitory Potential of Attenuated *Streptococcus pneumoniae* Strain THpep27 Against Inflammatory Disease, Respiratory Viral Infectious Disease, or Infectious Disease Caused by Bacteria Other than *Streptococcus pneumoniae*

1. Materials and Methods

Preparation of Attenuated *Streptococcus pneumoniae* Strain THpep27

The *Streptococcus pneumoniae* THpep27 mutant strain used in the Examples of the present disclosure is the strain reported by Choi S Y et al. (Inactivated pep27 mutant as an effective mucosal vaccine against a secondary lethal pneumococcal challenge in mice. Clin Exp Vaccine Res. 2013), which is the same as the pep27-mutated *Streptococcus pneumoniae* disclosed in Korean Patent No. 10-1252911, with the exception that erythromycin resistant marker (ermAM) for selection is not comprised.

A Cheshire cassette (GenBank accession No. FJ981645) carrying the erythromycin-resistance marker (ermAM), which can be used as a temporary marker for selection, was amplified using primers (5'-TGG CTT ACC GTT CGT ATA G-3' (SEQ ID NO: 2) and 5'-TCG ATA CCG TTC GTA TAA TGT-3' (SEQ ID NO: 3)), which were granted by Dr. Donald Morrison (University of Illinois at Chicago), and ligated by polymerase chain reaction (PCR), with upstream and downstream sequences amplified with primers (5'-TCT CTA TCG GCC TCA AGC AG-3' (SEQ ID NO: 4) and 5'-CTA TAC GAA CGG TAA GCC A GAT TTT CAC TGC TTT CG-3' (SEQ ID NO: 5), and 5'-ACA TTA TAC GAA CGG TAT CGA AAG GCC AGC AAG AGA CTA-3' (SEQ ID NO: 6) and 5'-CTG CGA GGC TTG CAC TGT AG-3' (SEQ ID NO: 7) from the genomic DNA of D39, which served as a template. Subsequently, the ligated product was then transformed into D39 to create a pep27 mutant.

Cheshire cassette excision was induced by adding 1% L-fucose (Sigma, St. Louis, Mo., USA). The fucose-treated cultures were then spread on THY blood agar plates to form single colonies. The presence of the Cheshire cassettes in each colony was confirmed by PCR using the following primers: 5'-TCT CTA TCG GCC TCA AGC AG-3' (SEQ ID NO: 8) and 5'-CTG CGA GGC TTG CAC TGT AG-3' (SEQ ID NO: 9). The mutant (THpep27) sequence was confirmed by nucleotide sequencing (Cosmo, Seoul, Korea) as well as by immunoblot analysis with Pep27 antibody (data not shown).

To confirm the THpep27 mutant at the RNA level, RNA was isolated from bacteria in the early exponential phase by using the conventional hot phenol method. After removal of DNA by DNase I (Takara, Tokyo, Japan), one microgram of bacterial RNA was reverse-transcribed into cDNA by using random primers (Takara). Reverse transcription PCR was performed by using recommended primer according to the manufacturer's instructions (Super Bio, American Building Restoration Products Inc., Franklin, Wis., USA).

Preparation of Other Bacterial Strains *Streptococcus pneumoniae* strains used in the present disclosure are summarized in Table 1, below.

TABLE 1

| strain | Characteristics | citation |
|---|---|---|
| D39 | encapsulated type, Serotype 2 | (Avery et al., 1944) |
| A66.1 | Serotype 3 | (McDaniel et al., 1984) |
| TIGR4 | Serotype 4 | (Aaberge et al., 1995) |
| BG7322 | Serotype 6B | (Briles et al., 1992) |
| THpep27 | D39 Δpep27:: Cheshire ermB Em$^r$ | (Choi et al., 2013) |

*S. pneumoniae* serotype 2 (D39) wild-type strain, serotype 3 (A66.1), serotype 6B (BG7322), and THpep27 mutant strain (D39 Δpep27) were cultured in the manner typically used in the lab (Kim et al, 2012). *Streptococcus pneumoniae* was cultured overnight at 37° C. on blood agar plates and then at 37° C. for 3 hours in Todd-Hewitt broth supplemented with 0.5% yeast extract (THY; Difco Laboratories). Each of the cultures of the *Streptococcus pneumoniae* strains was properly diluted and infected intranasally (i.n.) in an amount of 10 μl into CD1 mice.

*S. aureus* (ATCC 25923) and *K. pneumoniae* (ATCC 9997), which were purchased from the Korean Culture Center of Microorganisms (KCCM, Seoul), were cultured overnight at 37° C. in defibrinated sheep blood-supplemented brain heart infusion (BHI) broth and then transferred to fresh BHI broth in which the bacteria was cultured at 37° C. till $OD_{550}$=0.5.

Influenza virus A/California/04/2009(H1N1) strain was cultured in eggs as described previously (Shim et al, 2013).

In Vivo Infection Studies

Four-week-old male CD1, BALB/c mice (Orient, Korea) were used for infection experiments. The use of animals in the experiments was approved by Sungkyunkwan University Animal Ethical Committee in accordance with the guidelines of the Korean Animal Protection Law.

In a vaccine efficacy assay, mice were vaccinated intranasally (i.n.) with $1\times10^7$ to $1\times10^8$ CFU of Δpep27 strain every one or two weeks for a total of three times for measuring survival time. One to two weeks after the final immunization, the mice were intranasally challenged with $1\times10^7$ to $1\times10^8$ virulent D39 or 6B strain. The challenged mice were monitored for survival four times a day for the first five days, two times a day for the next five days, and once a day for up to 14 days after being challenged.

To evaluate colonization inhibiting ability, mice were intranasally inoculated with $1\times10^7$-$1\times10^8$ CFU of Δpep27 strain every two weeks for a total of three times. One to two weeks after the final vaccination, the mice were infected with $5\times10^6$-$1\times10^7$ CFU of *Streptococcus pneumoniae*. After sacrifice of the mice at predetermined times, the larynges were aseptically removed therefrom and homogenized using a homogenizer (PRO Scientific Inc., Oxford, Conn., USA, Model 200 Double insulated) at a maximum speed in 1 ml PBS (exclusive of blood) on ice and serially diluted in sterile PBS. The dilutions were spread on blood agar plates comprising 5-10 μg/ml gentamycin so as to select *Streptococcus pneumoniae*. Subsequently, the plates were incubated at 37° C. for about 18 hours in the atmosphere of 95% air-5% $CO_2$ to count colonies formed. This experiment was conducted twice and mean measurements of the experiments were used.

In order to examine whether the Δpep27 vaccine could protect against the infection of *S. aureus* and *K. pneumoniae*, mice were immunized intranasally three times with Δpep27. Ten days after the last Δpep27 immunization, the mice were intranasally infected with a suspension of $1\times10^8$ or $2\times10^6$ CFU of *S. aureus* or *K. pneumoniae* in 50 μl of PBS.

Subsequently, at 24 and 48 hours after being infected, pulmonary and nasal lavages were collected, homogenized, and serially diluted to a suitable extent. The serial dilutions were spread on BHI blood agar plates and cultured overnight at 37° C. for cell counting.

Experiment for Infection with Virus and *Streptococcus pneumoniae*

Mice (BALB/c male, 6-8 weeks old, Koatech, Korea) were immunized with a suspension of about $1\times10^8$ CFU of Δpep27 in 50 μl of PBS weekly for a total of three times. Ten days after the last immunization, the mice were intranasally infected with a suspension of H1N1 influenza virus in 50 μl of PBS at a lethal dose (LD) of 0.02, followed by monitoring body weights daily. At 10-12 days after influenza infection, the mice were intranasally infected with a suspension of $1\times10^8$ CFU of D39 in 50 μl of PBS and measured for survival rate.

Isolation of Splenocytes

Mice were intranasally immunized with $1\times10^7$ to $1\times10^8$ CFU of Δpep27 (THpep27 mutant strain) every two weeks for a total of three times. One week after the last immunization, the spleen was excised and the splenocytes thus obtained were treated with anti-CD3e (5 μl/ml; eBioscience) and anti-CD28 (3 μl/ml; eBioscience) antibodies in order to stimulate T lymphocytes (Bashour et al., 2014). After 24 hours of incubation, the cells were harvested and the culture media were measured for cytokine levels.

Cytokine Measurement

Levels of interleukin (IL)-17, tumor necrosis factor (TNF)-α, interferon (IFN)-γ, IL-4, and IL-10 in bronchoalveolar lavage (BAL), sera, and splenocytes were measured using an enzyme-linked immunosorbent assay (ELISA) kit (BD Biosciences, San Diego, Calif., USA) according to the manufacturer's instructions.

IgG Antibody Titer and Ig Subtype Determination

Mice were intranasally immunized with $1\times10^7$ to $1\times10^8$ CFU of Δpep27 every two weeks for a total of three times. Seven days after the last immunization, serum samples were obtained by retro-ocular bleeding and stored at −80° C. until ELISA. Antibodies were tittered as described previously (Roche et al., 2007; Kim et al., 2012; Cohen et al. 2013) and Ig subtypes were determined using a mouse Ig isotyping ELISA kit (eBioscience, USA).

In co-infection studies, IgG titers of sera were measured by ELISA method using 96-well immunoplates coated with *Streptococcus pneumoniae* lysates (D39, A66.1, and BG7322) or serotype 2 capsules, or PspA protein (1 μg/ml) purified in PBS (Kim et al., 2012; Cohen et al., 2013).

Virus and Bacteria Count in Lung

After intranasal immunization with Δpep27, mice (BALB/c four/group) were infected with H1N1 or H3N2 influenza virus as described above. Thereafter, pulmonary samples were collected and analyzed as reported previously (Shim et al, 2013).

Five days after influenza virus infection, the murine lungs were pushed through a 70 μm strainer, followed by centrifugation. The supernatant thus obtained was stored at −80° C. until titration. For viral titration, a suspension of MDCK cells in MEM (1% IgG-free BSA, 1× penicillin-streptomycin) medium was seeded at a density of $2\times10^4$ cells/well in 96-well plates which were then incubated at 37° C. for 4 hours. Afterwards, the cultured cells were infected with 2-fold serial dilutions of the lung homogenate supernatant and incubated overnight. Then, after the supernatant was discarded, virus titer was determined using anti-influenza A antibody with $TCID_{50}$/ml (Wu et al, 2015).

Real-Time PCR

From peritoneal macrophages that had been isolated and cultured, total RNA was isolated using RNAiso plus (TAKARA, Japan). RT-PCR was performed using one-step RT qPCR kit (Enzynomics, Korea). Gene-specific primer sequences were as follows: IL-10 gene (Forward [F]: 5'-AGC CAC CTC ATG CTA GAG C (SEQ ID NO: 10), Reverse [R]: 5'-GCC TGG TCT GGC ATC ACT AC (SEQ ID NO: 11)); IL-1β gene (F: 5'-CTG GTG TGT GAC GTT CCC AT (SEQ ID NO: 12), R: 5'-TGT CGT TGC TTG GTT CTC CT (SEQ ID NO: 13)); and TNF-α gene (F: 5'-CAC AAG ATG CTG GGA CAG TGA (SEQ ID NO: 14), R: 5'-TCC TTG ATG GTG CAT GA (SEQ ID NO: 15)). A GAPDH gene (primer F: 5'-TGC ATC CTG CAC CAA (SEQ ID NO: 16), R: 5'-TCC ACG ATG CCA AAG TTG TC (SEQ ID NO: 17)) was used as a control.

PCR program was performed as follows: Holding; 95° C., 10 min; 40 cycles of 95° C., 15 sec; 55° C., 30 sec, and 72° C., 30 sec; melting curve (95° C. 15 sec; 60° C., 1 min; 95° C., 15 sec).

High-Throughput Sequencing

In order to measure gene expression induced in the lung and spleen after immunization with Δpep27, mice (Balb/c 4-week-old) were intranasally vaccinated with $1\times10^7$-$1\times10^8$ CFU of *Streptococcus pneumoniae* Δpep27 (THpep27: Choi et al., 2013) without anesthesia every two weeks for a total of three times. RNA was isolated from lungs and spleens with the aid of Trizol reagent (Invitrogen) and sequencing libraries were constructed using 500 ng of the total RNA. For use in subsequent sequencing, an RNA library was constructed using a LEXOGEN Quant-Seq library preparation kit (Cat #001.24) according to the standard protocol. Gene expression was measured by high-throughput sequencing using Illumina NextSeq 500.

DNA Treatment Step

Base calling was accomplished using Illumina Casava1.8 Software. Sequence reads were arranged for the adapter sequences, followed by filtering out low-complexity and low-quality sequence reads with the aid of fastx_trimmer. The resulting reads were mapped to the full mm10 genome, using Bowtie2. Read count extraction and data normalization were implemented using edgeR. Experiments and system biology analysis using Ingenuity Pathway Analysis were conducted in e-Biogen (Seoul, Korea).

Gene expression analysis data was deposited with NCBI [GEO accession number GSE93718] (http://www.ncbi.nlm.nih.gov/geo/).

Measurement of Protective Potential Against Inflammatory Bowel Disease

Figure 29:
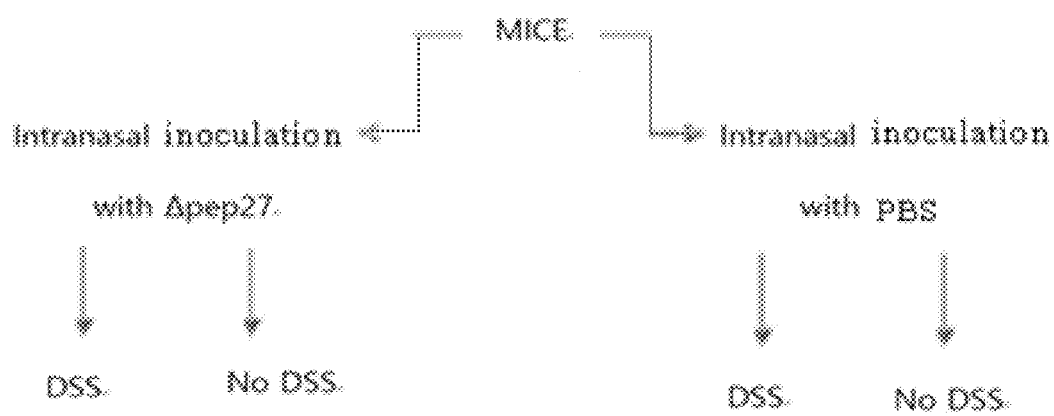
FIG. 29 illustrates experimental groups of mice used in a series of experiments for an assay of ΔPep27 immunization for inhibition against DSS-induced enterocolitis in mice in accordance with one embodiment of the present disclosure.

After being anesthetized by intraperitoneal injection of with 100 μl of ketamine, mice (C57BL/6 male, 4-week-old) were intranasally vaccinated with $1\times10^7$ to $1\times10^8$ CFU of Δpep27 weekly for a total of three times. The mice were measured for body weight and randomly divided into four experimental groups of two per group. Referring now to FIG. 29, the experimental groups of mice used in a series of experiments were as follows: a control not treated with dextran sulfate sodium (DSS), an experimental control treated with 5% DSS alone, an experimental group immunized with Pep27 alone, and a group to which Pep27+5% DSS were administered. Mice were fed with DSS (5%, w/v) having an average molecular weight of 5000 (Sigma Chemical Co., St. Louis, Mo., USA) for 14 consecutive days to induce enterocolitis (Wirtz et al, 2007). In this regard, the DSS solution was daily exchanged with a fresh one. Mice in the control group were allowed to drink tap water only.

All mice in the control group and experimental control group were administered a vehicle (saline) in amounts equivalent to those for the DSS-administered group as the same way as the DSS-administered group for the study duration.

Inflammatory Bowel Disease (IBD) Sampling

Fourteen days after administration of 5% DSS, experimental animals were euthanized by $CO_2$ asphyxiation, followed by performing laparotomy. The entire large intestine ranging from the caecum to the anus was removed and divided into proximal, middle, and terminal portions. The selected tissues were separated, then washed with phosphate buffered saline (PBS), and stored at −80° C. until analysis.

Quantitation of Colon Fragments (Disease Activity Index: DAI)

The progression of colitis was daily evaluated by measuring drinking amount, weight loss, stool consistency, rectal bleeding, and the presence of total blood in stool. Also, clinical symptoms were evaluated. The mice were also monitored daily for morbidity (weariness and lethargy).

These parameters were scored according to the criteria suggested below, which were used to calculate mean daily disease activity index (DAI) for each animal as suggested in the previous reports (Wirtz et al, 2007; Jawhara and Poulain, 2007).

In addition, large intestine inflammation was evaluated by measuring the length of the colon which remained unstretched and ranged from the sigmoid junction to the anal margin, with the naked eye. Detailed pathogenic opinions were given for each group. A system in which tissues were visually scored 0 to 5 points was used to evaluate the time when the organ affected by the most severe inflammation underwent a change and the extent of the change.

The pathological scoring system verified previously (Jawhara and Poulain, 2007; Xu et al, 2007) was modified to evaluate the colitis. All experiments were repeated at least twice and calculated for all groups as follows:

1) Weight loss: no change, 0; <5%, 1; 6-10%, 2; 11-20%, 3; >20%, 4;

2) Stool consistency: normal or well-formed pellet, 0; dough-shaped bandages shapes that do not stick to the anus(not sticky, pasty, semi-formed), 1; sticky liquid that remain attached to the anus, 2; sticky with some blood, 3; completely liquid, bloody, or unable to defecate after 10 min, 4;

3) Rectal bleeding: no blood, 0; visible blood in anus or rectum, 1; visible blood on fur, 2; significant bleeding from rectum, 4;

4) General appearance: normal, 0; mucous, 1; lethargic and piloerect, 2; lethargic and hunched, 3; motionless and sick, 4.

Statistical Analysis

All data were expressed as the mean values of independent duplicate measurements ±standard deviation. Statistical comparison was conducted by one-way ANOVA followed by Bonferroni's test. All P-values <0.05 were considered significant.

2. Results 2-1. Case #1: HTS and system biology analysis indicates a protective function against main lesions.

2-1-1. ΔPep27 Immunization Protected Mice Against Various Lesions.

Figure 2:
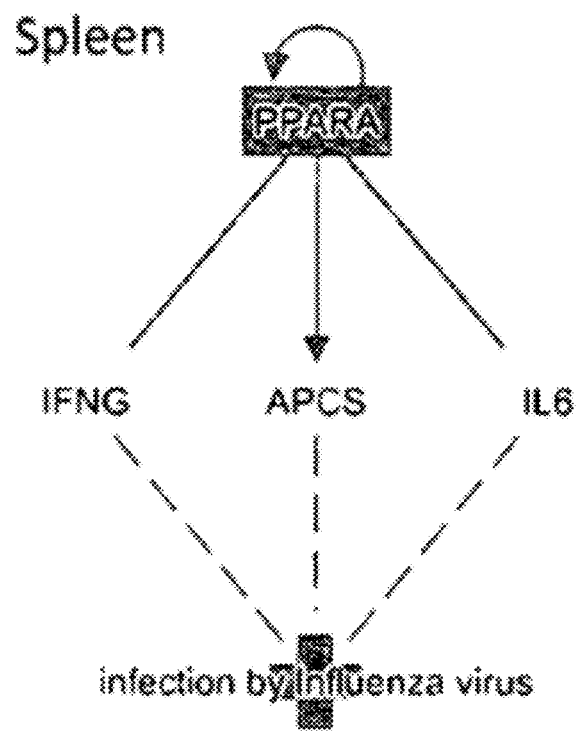

System biology analysis in the lung indicates that intranasal immunization with Δpep27 protects against gastroenteritis and prevents the large intestine from turning abnormal (FIG. 1). In addition, system biology analysis in the spleen shows that Δpep27 immunization protects against infection by influenza virus (FIG. 2).

2-1-2. ΔPep27 Immunization Induced Treg Cells.

Figure 3:
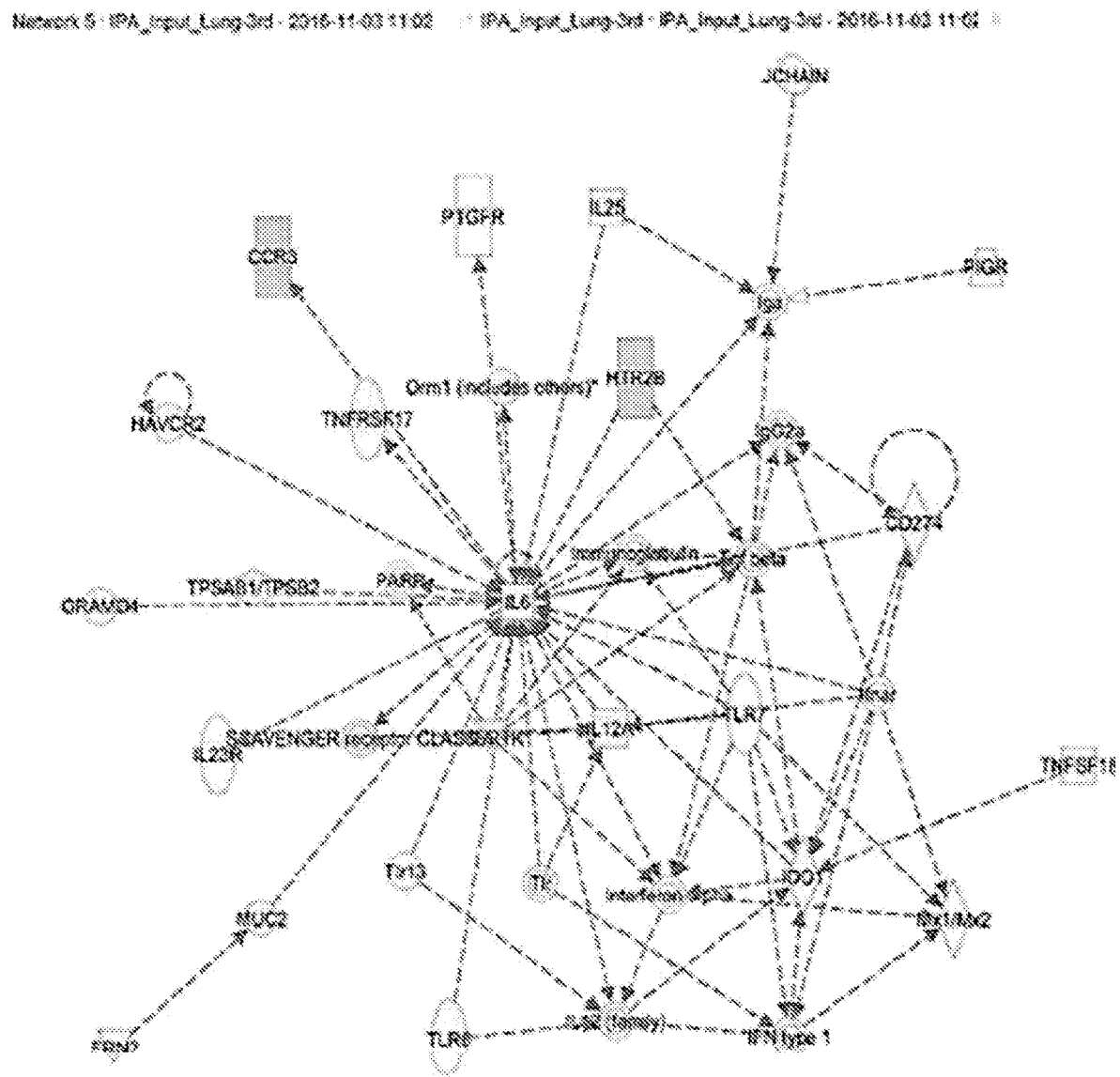
FIG. 3 is a schematic diagram of a system biology analysis result in the lung according to one embodiment of the present disclosure. Mice were intranasally inoculated with Δpep27 mutant strain every two weeks for a total of three times. On day 7 after the last immunization, mRNA was isolated from the lung and subjected to high-throughput sequencing. IPA network analysis for sequence data in the lung is depicted, accounting for the induction of IL-6, IL-23R, MUC2, IFN type 1, and TGF beta, as well as the downregulation of CCR3.
Figure 4:
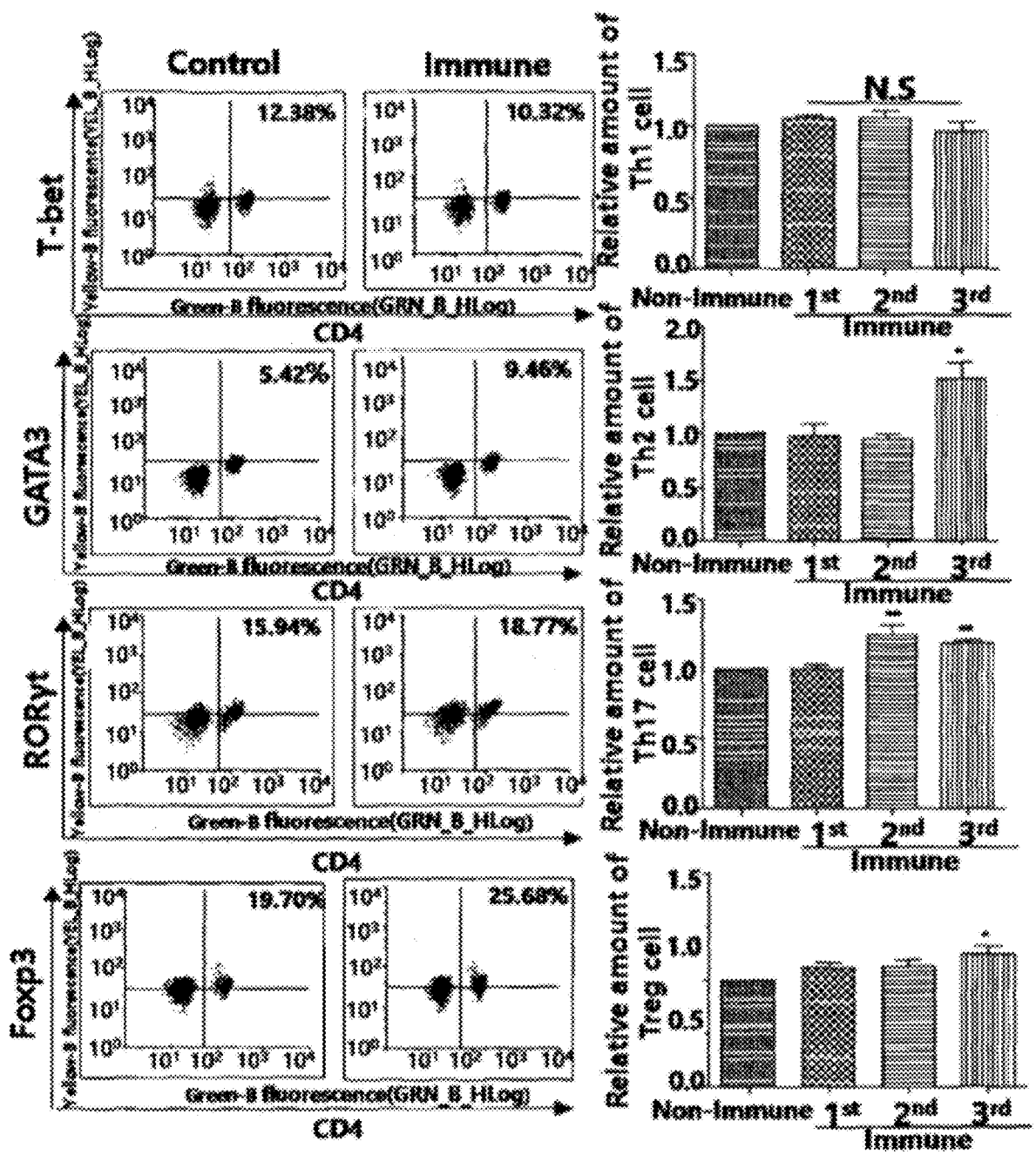
FIGS. 4 to 6 show data from an experiment for examining whether Δpep27 immunization could induce Treg cells in mice in accordance with one embodiment of the present disclosure.
Figure 5:
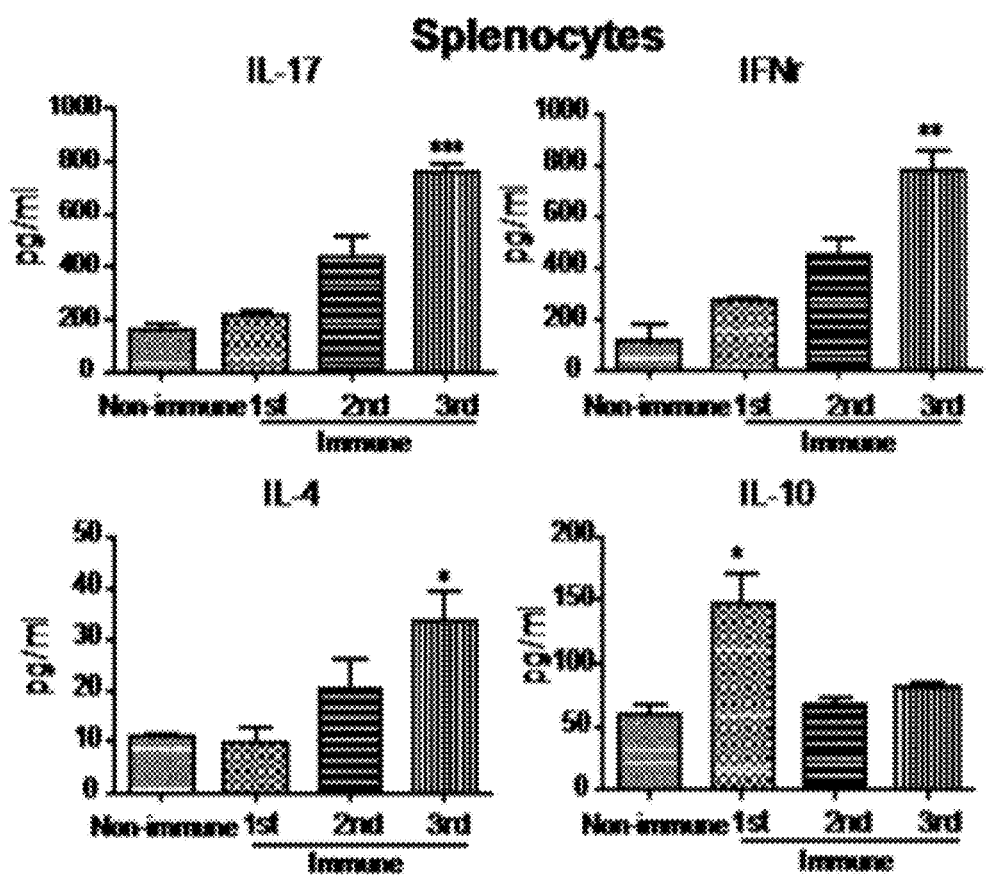
Figure 6:
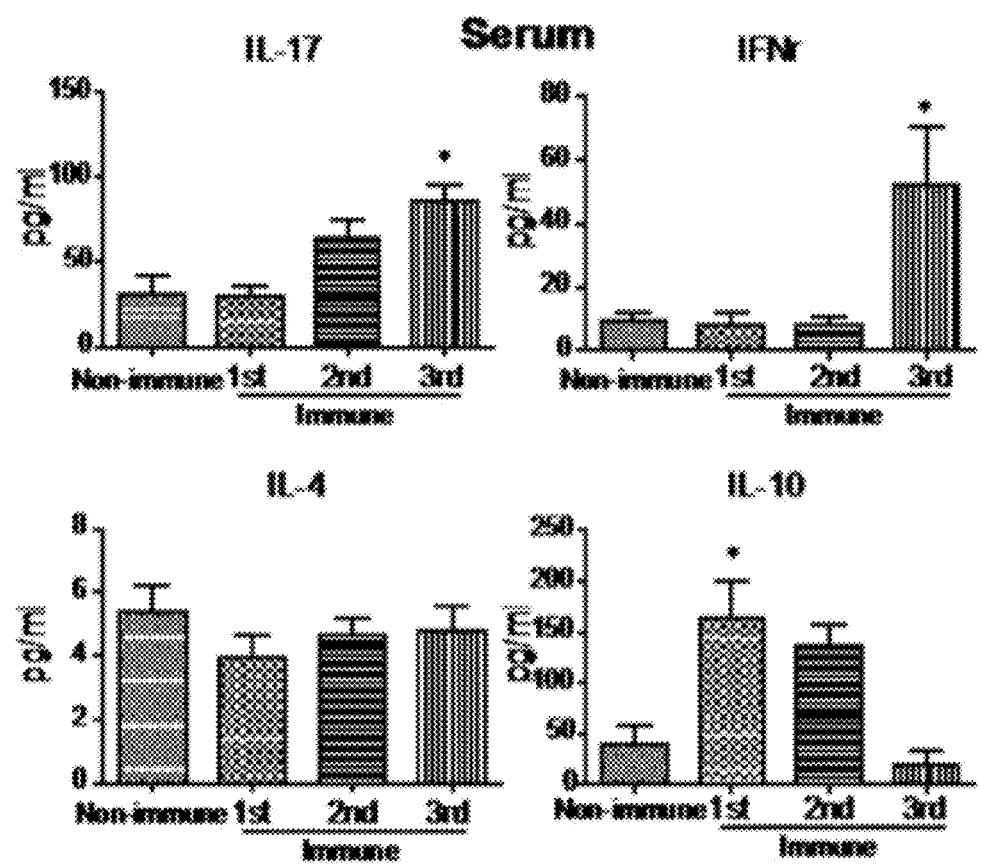

System biology analysis in the lung also shows that Δpep27 immunization induces the expression of TGF-β in the lung (FIG. 3). In FIG. 3, green accounts for the suppression of gene expression while red means the induction of gene expression. To confirm the Treg induction by Δpep27 inoculation, splenocytes of the mice inoculated were analyzed by FACS. As can be seen, Δpep27 immunization increased Th2, Th17, and Treg cell populations, but Th1 cells remained almost unchanged (FIG. 4), suggesting that such induced Treg cells play a certain role in immune tolerance. In order to support the induction of Treg, levels of cytokines in splenocytes and sera were measured. Consistent with the foregoing, significant induction was made of interferon (IFN)-γ, IL-4, IL-17, and IL-10 in the spleen (FIG. 5). In addition, significant induction of IFN-γ, IL-17, and IL-10 was also observed in sera, but with no significant changes in IL-4 level detected (FIG. 6). These results implied that the induction of Treg cells leads to the production of the anti-inflammatory cytokine IL-10, thus reinforcing immune tolerance.

2-1-3. IL-10 Induction by ΔPep27 Immunization

Figure 7:
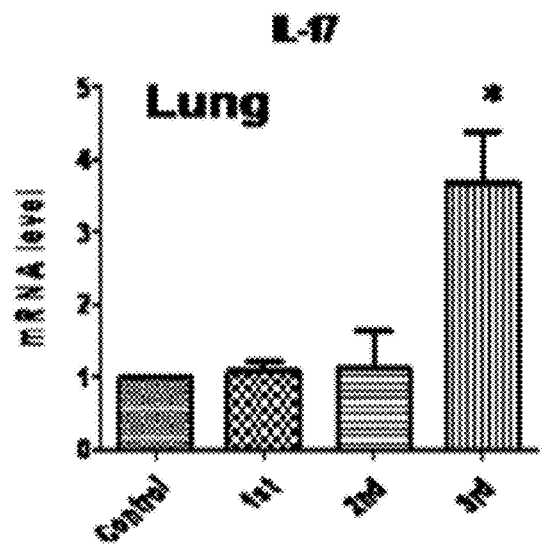
FIGS. 7 and 8 present data from an experiment in which mice were immunized with Δpep27 to induce IL-10 and IL-17 in accordance with one embodiment of the present disclosure. Mice (n=3) were immunized by inoculating intranasally with Δpep27 every two weeks for a total of three times. On day 7 after the last immunization, mRNA was isolated from the lung and used to measure expression levels of IL-17 (FIG. 7) and IL-10 (FIG. 8) genes by qPCR. Statistical significance was analyzed by ANOVA; *, P<0.05.
Figure 8:
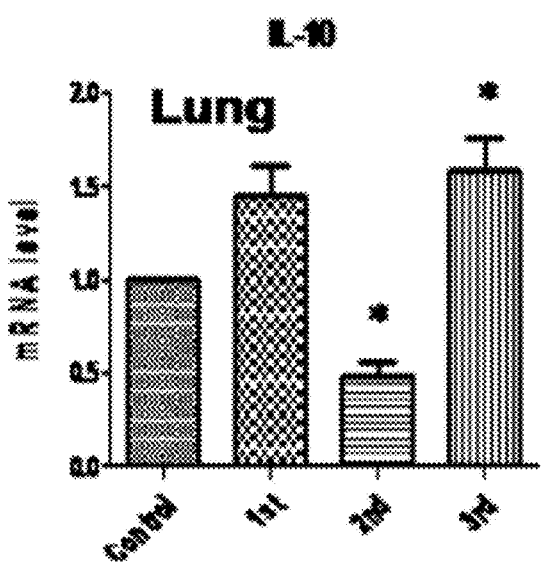

In order to support the immune tolerance response, pulmonary and bronchoalveolar lavage (BAL) fluid was measured for IL-10 and IL-17 mRNA levels. Consistently, Δpep27 immunization increased significantly mRNA levels of both IL-10 and IL-17 in the lung (FIGS. 7 and 8).

2-1-4. Induction of Memory Response by ΔPep27 Immunization

Figure 9:
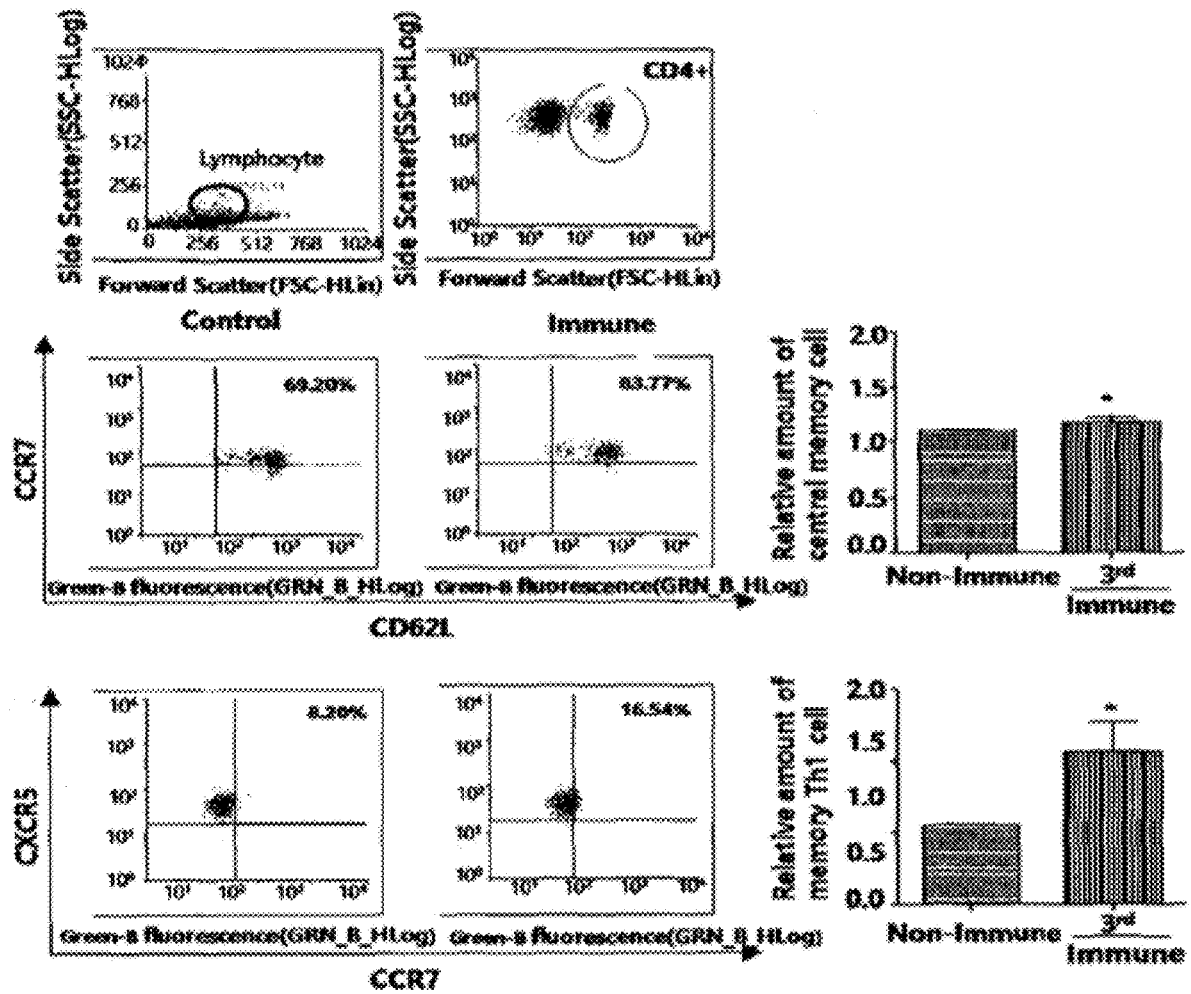
FIG. 9 shows data from an experiment in which mice were immunized with Δpep27 to activate central memory T cells and memory Tfh cells in the spleen according to one embodiment of the present disclosure. Mice (n=3) were intranasally immunized with Δpep27 every two weeks for a total of three times. On day 7 after the last immunization, splenocytes were isolated and labeled with fluorescent cell markers against central memory T cells (CD4, CCR7, CD62L) and memory Tfh cells (CD4, CXCR5, CCR7). Subsequently, the fluorescent markers were detected by flow cytometry. Statistical significance was analyzed by ANOVA; *, P<0.05.

To examine whether intranasal vaccination evokes a memory response, splenocytes were harvested from immunized mice and analyzed for memory responses. As a result, Δpep27 immunization increased populations of central memory T cells (CD4, CCR7, CD62L) and memory Tfh cells (CD4, CXCR5, CCR7) in spleen (FIG. 9).

Figure 10:
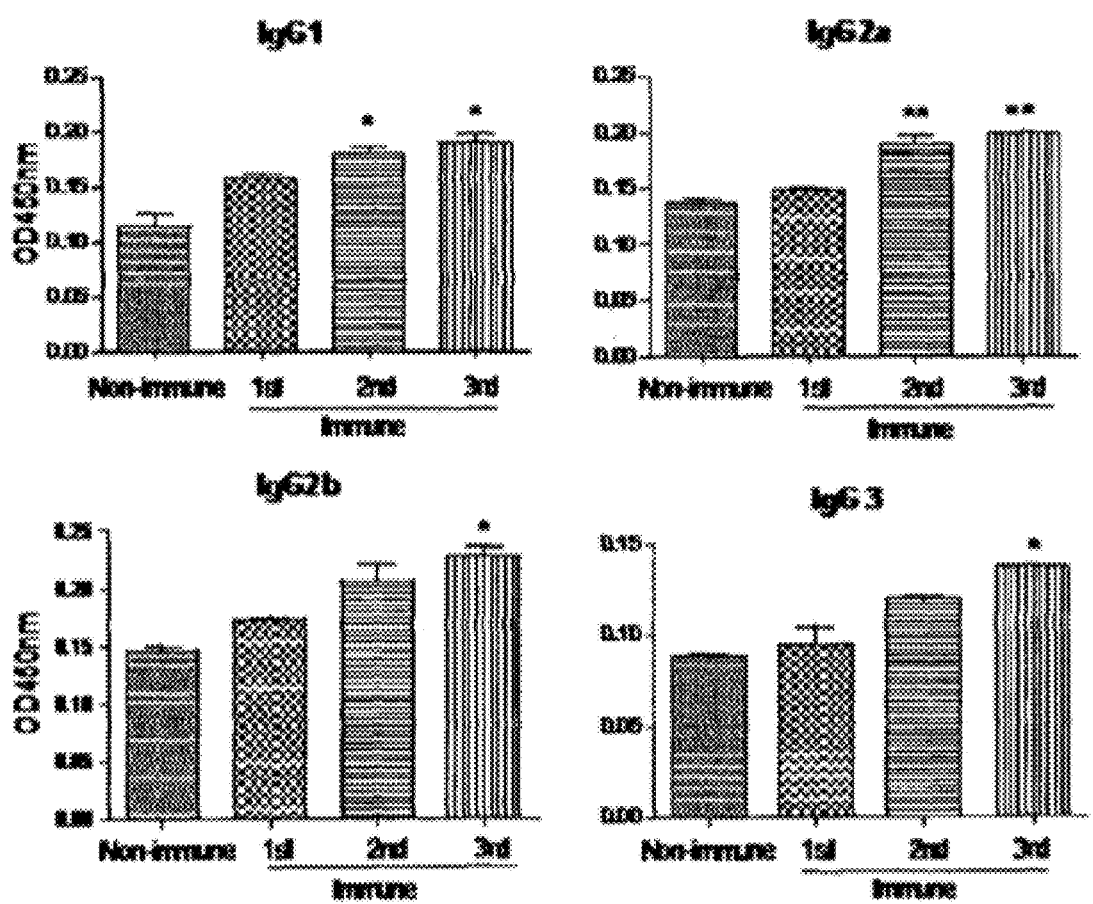
FIGS. 10 and 11 present data from an experiment in which mice were immunized with Δpep27 to induce the expression of various immunoglobulin subtypes according to one embodiment of the present disclosure. Mice (n=6) were intranasally immunized with Δpep27 every two weeks for a total of three times. On day 7 after the last immunization, sera (FIG. 10) and bronchoalveolar lavage (BAL) fluid (FIG. 11) were measured for antibody titers against pneumococcal whole cells of three types. Statistical significance was analyzed with ANOVA; * P <0.05, **, P<0.01.
Figure 11:
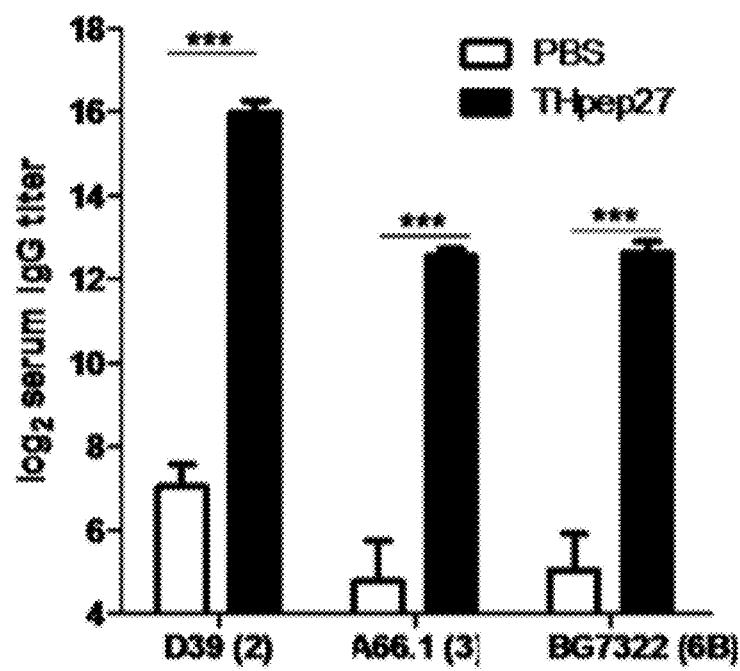

In order to confirm the memory response again, antibody titers of various serum immunoglobulin subtypes were measured. As expected, Δpep27 vaccine immunization induced expression of various immunoglobulin subtypes such as IgG1, IgG2a, IgG2b, and IgG3 (FIG. 10). In addition, level of IgG antibodies against pneumococcal whole cells of three types were also significantly increased by the vaccination (FIG. 11). Therefore, the intranasal vaccination was confirmed to induce a memory response.

2-2. Case 2: Protection Against Co-Infection by Influenza Viruses

Streptococcus pneumoniae and influenza A virus (IAV) are main causes of respiratory infection (Bosch et al, 2013, Shak et al, 2013). Streptococcus pneumoniae or IAV itself cause a respiratory disease, but mortality is increased by secondary infections following influenza virus infection (Mina and Klugman, 2013). However, the currently available pneumococcal polysaccharide conjugate vaccine, PCV 13, fails to effectively protect against secondary pneumococcal infection (Metzger et al, 2015).

Figure 12:
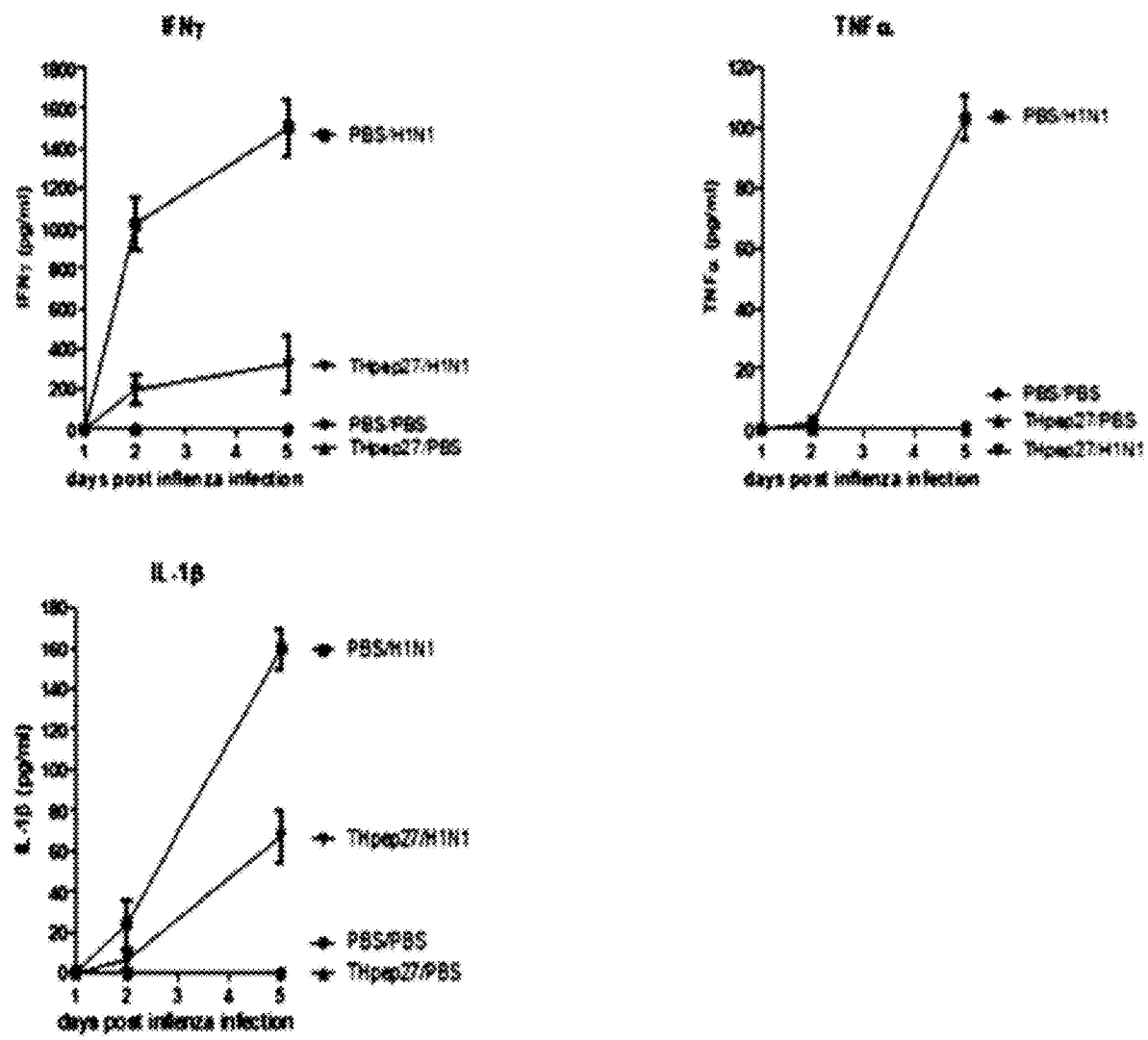
FIGS. 12 to 15 show data from an experiment for examining whether Δpep27 immunization could protect against secondary pneumococcal infection following influenza infection in accordance with one embodiment of the present disclosure. Mice (9-10/group) were immunized intranasally with Δpep27 weekly for a total of three times. One week after the last immunization, the mice were intranasally infected with influenza virus. Blood samples obtained by retro-ocular bleeding were then analyzed for cytokines (FIG. 12), or one week after the last immunization, sera were collected from the mice and analyzed for IgG levels for particular antigens by ELISA (FIG. 13). Significant differences between the two groups were analyzed by unpaired t-test; * p<0.001. Ten days after influenza infection, mice were infected with Streptococcus pneumoniae D39 via an intranasal route and then monitored for survival for 14 days (FIG. 14). Statistical significance was analyzed by Mentelcox test;  p<0.005. Twenty-four hours after Streptococcus pneumoniae D39 infection, lung homogenates were incubated in serum to count bacteria (FIG. 15). Statistical significance was analyzed by one-way ANOVA.
Figure 13:
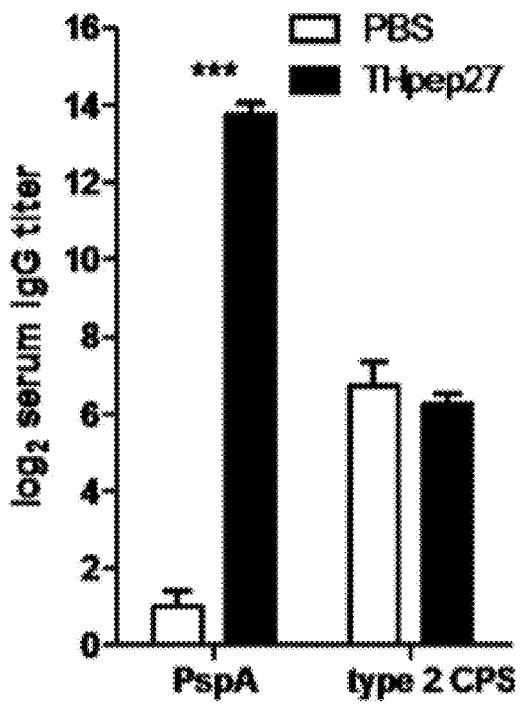

2-2-1. Protection by ΔPep27 Immunization Against Secondary Pneumococcal Infection Previously, it was shown that intranasal inoculation with Δpep27 could induce IgG and protect mice from heterologous pneumococcal infection (Kim et al, 2012). In this disclosure, analysis was made to see whether Δpep27 immunization could raise antibody titers against whole bacterial cells as well as specific antigens. Results showed that intranasal inoculation with Δpep27 increased IgG titers against strains of capsular serotypes 3 and 6B as well as serotype 2 (D39) whole cells. This increase was significantly higher than that in the non-immunized controls, indicating that Δpep27 immunization induced humoral immunity against both homologous and heterologous pneumococcal strains (FIG. 11). As concerns cytokine levels following influenza infection, all level of INF-γ, TNF-α, and IL-1β were measured to be significantly lower in immunized experimental groups than those in non-immunized controls, indicating that Δpep27 immunization induced immune tolerance (FIG. 12). When IgG titers against specific antigens such as PspA protein and serotype 2 capsular polysaccharide were determined, Δpep27 immunization increased antibody titers against PspA protein, but not serotype 2 capsular polysaccharide (FIG. 13).

Figure 14:
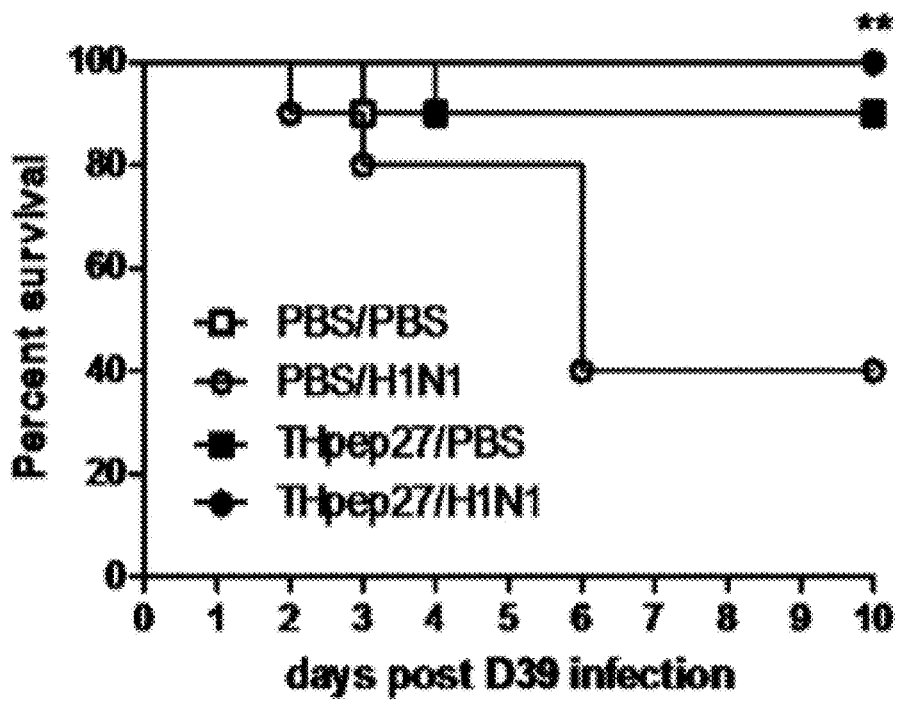

To investigate the protective effect of intranasal immunization with Δpep27 on secondary pneumococcal infection, mice were infected with 0.02 lethal dose ($LD_{50}$) of H1N1 influenza virus. Ten days post-influenza virus infection, mice were infected with the virulent pneumococcal strain D39, and the survival rate was monitored. While non-vaccinated mice (PBS/H1N1) succumbed to pneumonia after D39 infection, most nasally immunized mice (THpep27/H1N1) successfully survived after D39 infection (FIG. 14). This result suggests that intranasal immunization with Δpep27 could protect mice against secondary pneumococcal infection as well as against influenza virus infection.

Figure 15:
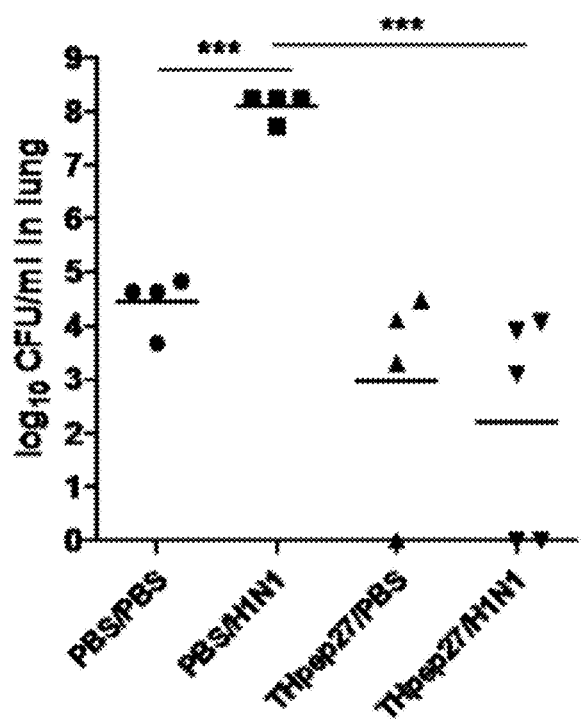

When mice were infected with *Streptococcus pneumoniae* post-intranasal immunization, far fewer bacteria were detected in the lung of all the vaccinated mice than non-vaccinated controls (FIG. 15), indicating that intranasal immunization with Δpep27 also successfully protected mice from secondary pneumococcal infection post-influenza infection.

2-2-2. Decrease of Viral and Bacterial Counts in Lung by ΔPep27 Immunization

Figure 16:
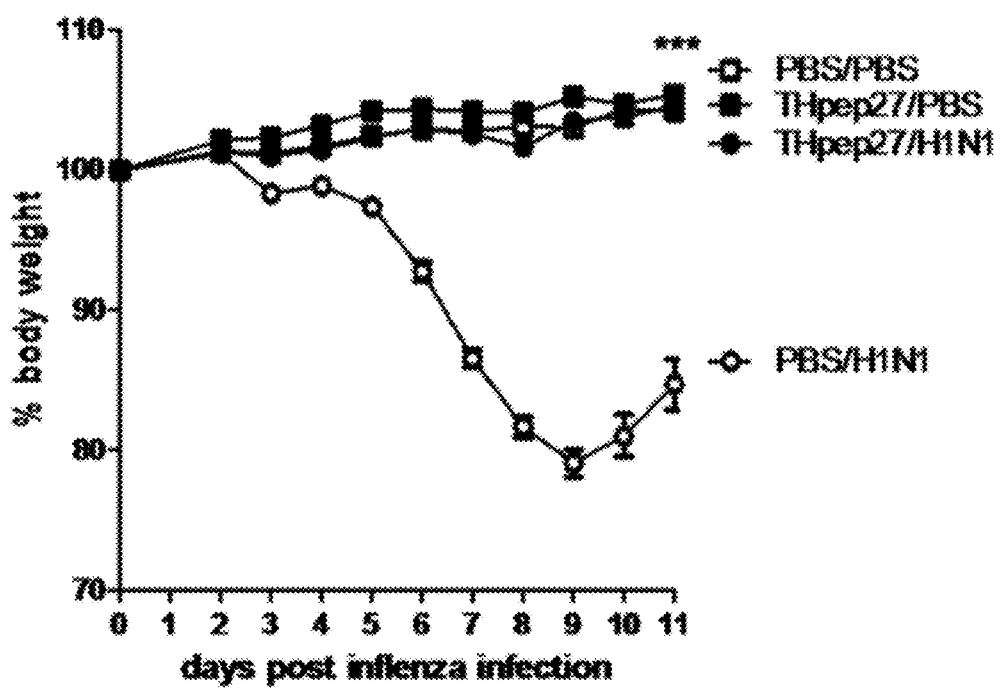
FIGS. 16 and 17 show data from an experiment in which a Δpep27 vaccine was tested for inhibitory activity against influenza virus replication in accordance with one embodiment of the present disclosure. Mice (10/group) were intranasally immunized with influenza virus and then monitored for body weight for 11 days (FIG. 16). Statistical significance was analyzed by one-way ANOVA; * p<0.001. Five days after influenza infection, lung homogenate supernatants were collected and then measured for virus titers in each group by determining $TCID_{50}$/ml (FIG. 17). Significance was analyzed by one-way ANOVA; * p<0.001.
Figure 17:
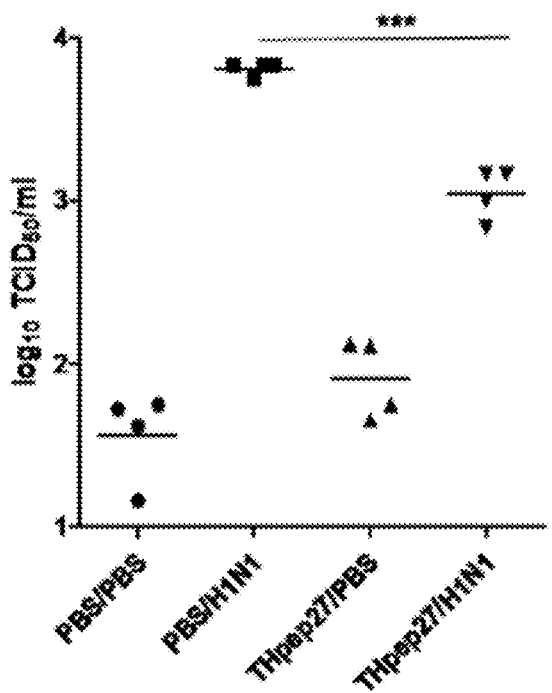

To investigate whether Δpep27 immunization attenuated the influenza virus load, body weight loss was determined after influenza virus infection. Interestingly, no mice vaccinated with Δpep27 underwent weight loss after influenza infection whereas the non-vaccinated mice showed significant weight loss (FIG. 16). Because Δpep27 vaccination protected against weight loss from influenza virus infection, additional examination was made to check whether Δpep27 vaccination could affect influenza virus replication in the lung by determining the $TCID_{50}$ of lungs from influenza-infected mice. Surprisingly, vaccinated mice showed significantly lower virus titers in the lung than non-vaccinated control mice (FIG. 17). These results indicated that intranasal vaccination with Δpep27 not only protected against pneumococcal infection, but also significantly alleviated influenza virus infection.

Figure 18:
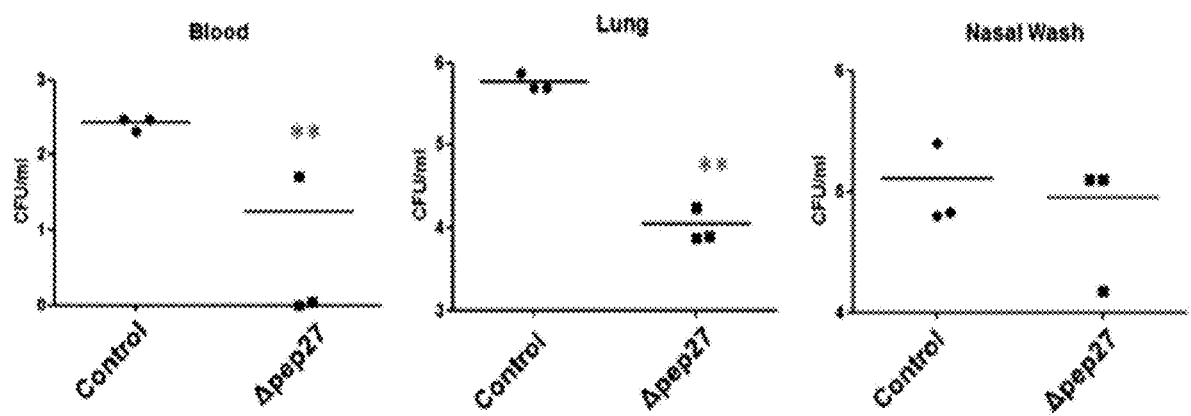
FIG. 18 shows data from an experiment for examining whether Δpep27 immunization could prevent Gram-negative bacterial infection in accordance with one embodiment of the present disclosure. Mice (3/group) were intranasally immunized with Δpep27 three times. Ten days after the last immunization, the mice were infected with K. pneumoniae. Bacterial counts in individual organs were determined 24 hours post-K. pneumoniae infection by spreading on blood agar plates; ** P<0.01.

2-3. Case 3: Protection by ΔPep27 Immunization Against Other Bacterial Infection 2-3-1. Protection by ΔPep27 Immunization Against Gram-Negative Bacterial Infection To investigate whether Δpep27 immunization could prevent colonization of other bacteria, mice were vaccinated with Δpep27 and then infected with the Gram-negative bacterium *Klebsiella pneumoniae*, followed by counting the bacteria in tissues. Twenty four hours post-infection, a significantly reduced count of *Klebsiella pneumoniae* was detected in the lungs and sera of the vaccinated groups, compared to non-vaccinated controls (FIG. 18). The data demonstrated that Δpep27 vaccination could prevent Gram-negative bacterial infection.

Figure 19:
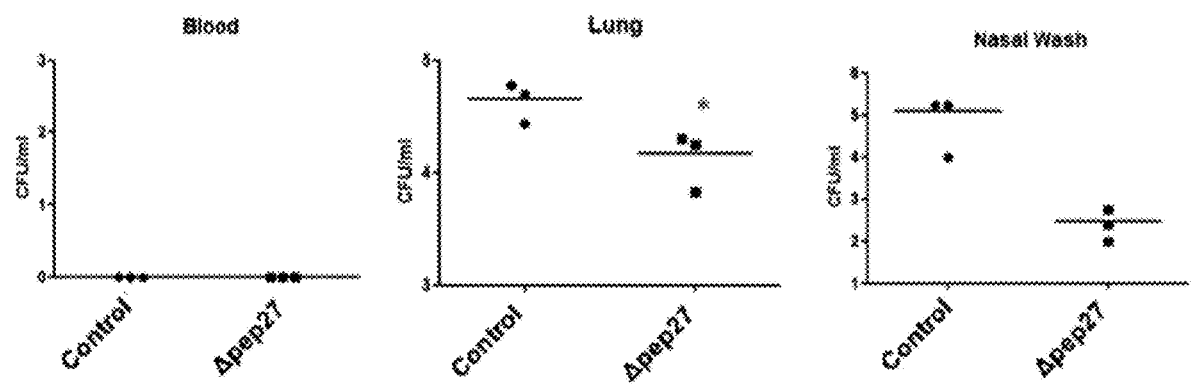
FIG. 19 shows data from an experiment for examining whether Δpep27 immunization could prevent Gram-positive bacterial infection in accordance with one embodiment of the present disclosure. Mice (3/group) were intranasally immunized with Δpep27 three times. Ten days after the last immunization, the mice were infected with Staphylococcus aureus. Bacterial counts in individual organs were determined 24 hours post-S. aureus infection by spreading on blood agar plates; * P<0.05.

2-3-2. Protection by ΔPep27 Immunization Against Gram-Positive Bacterial Infection To investigate again whether Δpep27 vaccination could prevent colonization of other bacteria, mice were vaccinated with Δpep27 and then infected with the Gram-positive bacterium *Staphylococcus aureus*, followed by counting the viable bacteria in tissues. Interestingly, significant fewer colonies were detected in pulmonary and nasal lavage fluid of Δpep27-vaccinated group than in non-vaccinated control (FIG. 19). This result demonstrated that Δpep27 vaccination could prevent the infection of other bacteria such as Gram-positive bacteria.

2-4. Case 4: Protection Against Inflammatory Bowel Disease

Oral immune tolerance phenomena have been studied for rheumatoid arthritis (RA), allergic disease, diabetes, arteriosclerosis, colitis diseases of human (Faria and Weiner, 2005). It was reported that intranasal inoculation with effector protein (SseB) derived from *Salmonella* induced intestinal and systemic IgA, Th1, and Th17 responses, after which bacterial burdens in intestinal tissues and the spleen were reduced even upon oral lethal infection (Pigny et al., 2016). However, nowhere have intranasal vaccines for protection against inflammatory bowel disease been reported previously.

2-4-1. Protection by ΔPep27 Vaccination Against Inflammatory Bowel Disease

Figure 20:
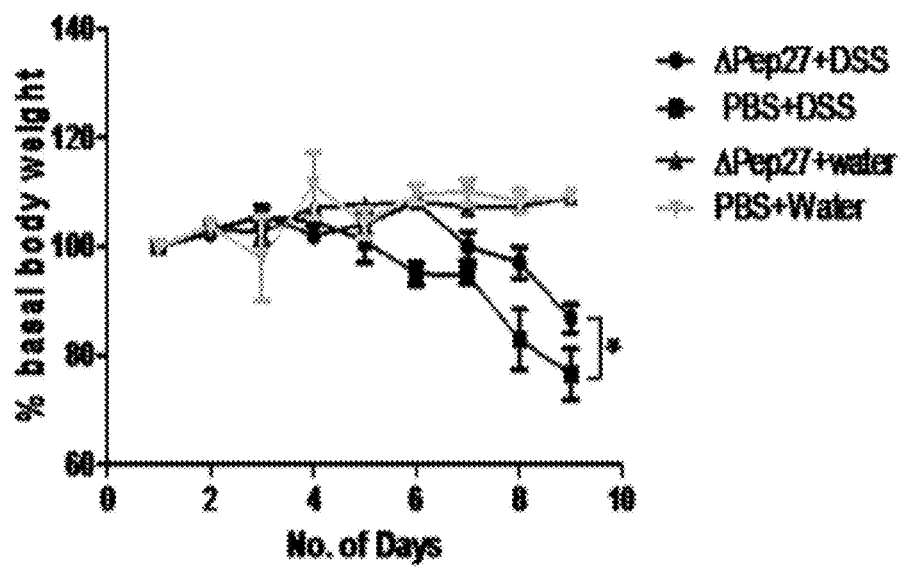
FIGS. 20 and 21 show data from an experiment for examining whether Δpep27 immunization could inhibit against the weight loss resulting from dextran sulfate sodium (DSS)-induced inflammatory bowel disease in accordance with one embodiment of the present disclosure. Mice (n=5/group) were intranasally immunized with Δpep27 mutant strain three times and then administered 5% DSS in drinking water via an oral route to induce colitis (inflammatory bowel disease) therein. The immunized mice were observed to undergo reduced weight loss (FIG. 20). In this regard, percentages of basal weight loss were monitored for 9 days after DSS treatment. Statistical significance was analyzed by one-way ANOVA, followed by conducting Bonferroni's test. Clinical disease activity index was evaluated daily until the therapy was ended on day 9 (FIG. 21). The progression of colitis was evaluated by measuring weight loss, stool consistency, rectal bleeding, and/or the amount of total blood in stool. Also, the mice were monitored daily for morbidity (piloerection and lethargy).

To investigate whether Δpep27 vaccination could suppress inflammatory bowel disease, mice were intranasally immunized with the vaccine, followed by inducing colitis with DSS. As a result of the experiment, the disease activity index was worsened from day nine after addition of 5% DSS to drinking water, with the concomitant significant reduction of body weight in the mice. While mice treated with 5% DSS alone underwent significant weight loss, the experimental group immunized with Δpep27 and treated with 5% DSS decreased significantly less in body weight than the group treated with DSS alone (FIG. 20).

Figure 21:
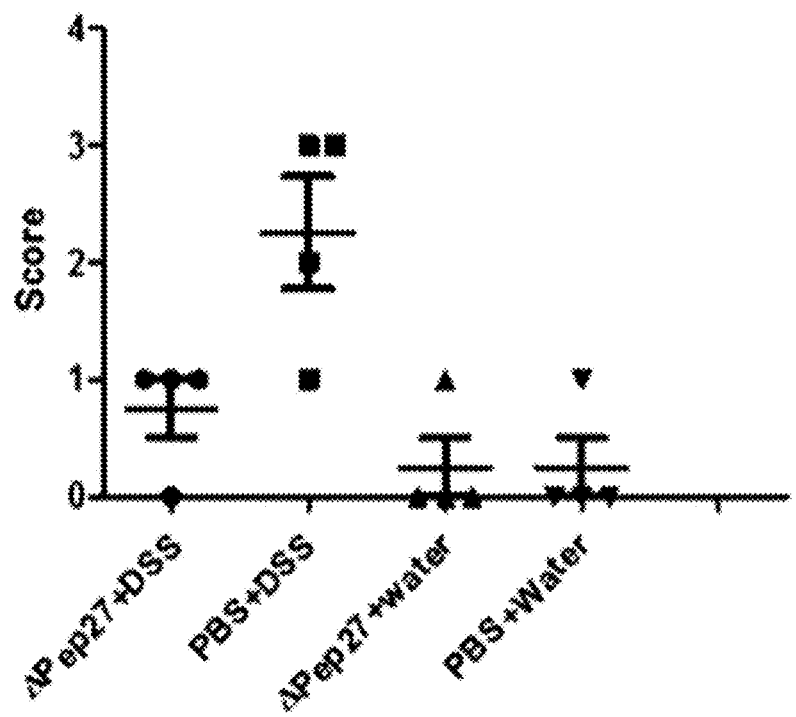

When overall clinical disease activity index scores ($p<0.05$, one-way ANOVA followed by Bonferroni's test, DSS treatment for 6-9 days) were compared, the group treated with 5% DSS alone scored significantly higher points for stool consistency than the experimental group treated with Δpep27+5% DSS (FIG. 21). Thus, the result indicated that after the onset of DSS-induced colitis, the disease was aggravated in the group treated with DSS alone, with a high clinical disease activity index given thereto whereas the colitis in the vaccinated group was as light as in the normal group.

Figure 22:
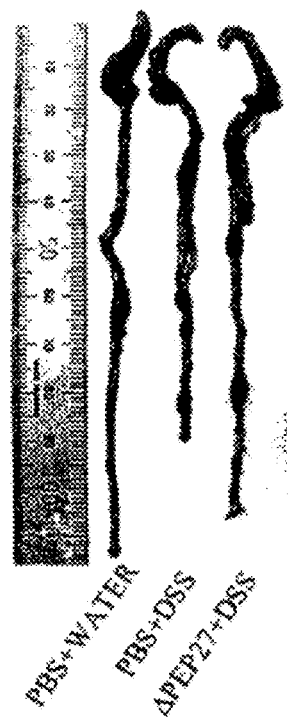
FIGS. 22 and 23 show data from an experiment for examining whether Δpep27 immunization could prevent dextran sulfate sodium (DSS)-induced colitis in accordance with one embodiment of the present disclosure. Mice (n=5/group) were intranasally immunized with Δpep27 three times and then administered 5% DSS in drinking water via an oral route to induce colitis (inflammatory bowel disease) therein. The immunized mice were observed to undergo reduced weight loss (FIG. 20). The colon was examined on day 9 post-DSS treatment. Colon length (FIG. 22) and weight (FIG. 23) were measured on day 9 post-DSS treatment.
Figure 23:
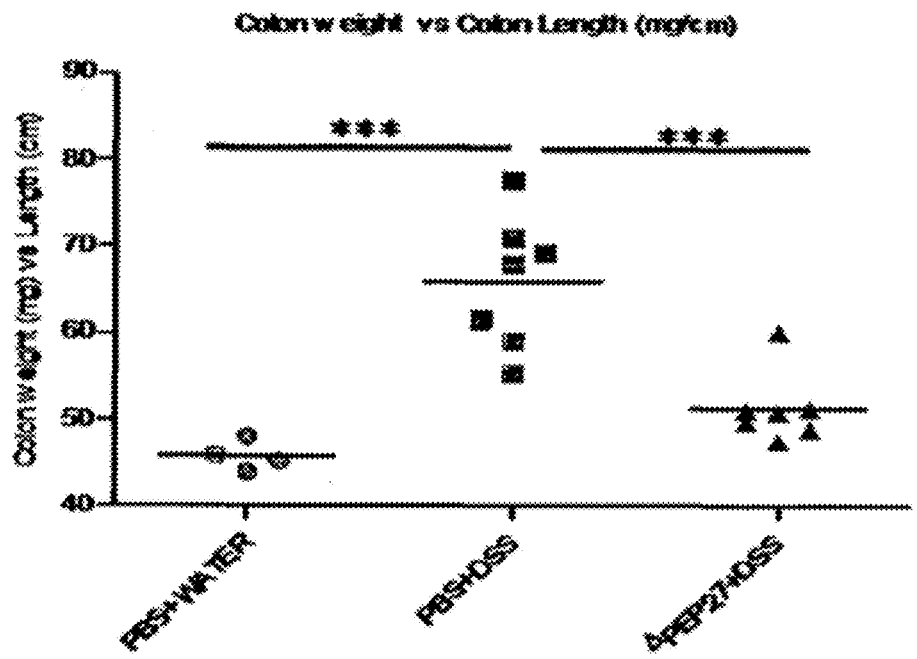

The reduction of colon length is used as an inflammation marker in DSS-induced colitis model. In practice, the colon length in DSS-administered groups was reduced with significance (FIG. 22). Accordingly, the DSS group significantly increased in the ratio of colon weight/colon length, but the Δpep27-vaccinated group exhibited an almost normal ratio, compared to the DSS group (FIG. 23).

2-4-2. Inhibition of Inflammatory Cytokines by ΔPep27 Vaccination

Figure 24:
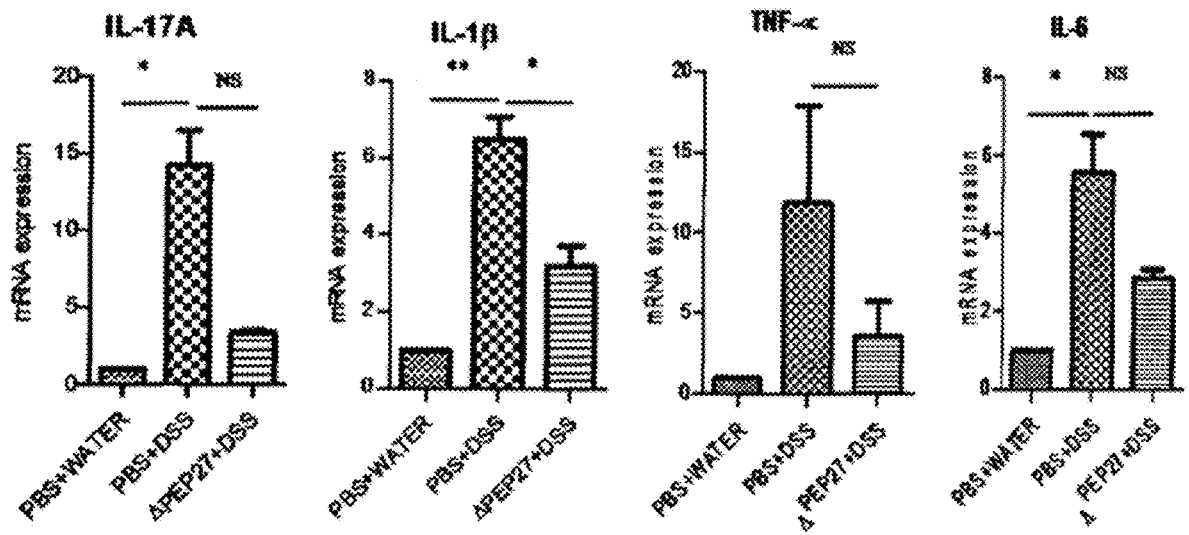
FIG. 24 shows data from one embodiment for examining whether Δpep27 immunization could suppress the expression of inflammatory cytokine genes in the large intestine in accordance with one embodiment of the present disclosure. Balb c mice were fed with 5% DSS in drinking water for 14 days to induce inflammatory bowel disease. PBS+water was used for a negative control. mRNA expression levels of IL-1β, IL-6, IL-17A, and TNF-α were measured by real-time quantitative PCR. Experimental data were expressed as mean±SEM. P<0.05 was considered significant.

To confirm the reductive effect of Δpep27 vaccination on intestinal inflammation, mRNA levels of cytokines in the large intestine were measured. As a result of the experiment, the Δpep27-vaccinated group was observed to have a significantly reduced mRNA level of pro-inflammatory IL-1β, compared to the non-immunized control (FIG. 24). In addition, the intranasal vaccination suppressed mRNA levels of IL-17A, TNF-α, and IL-6, compared to non-immunized control (FIG. 24), demonstrating that the intranasal vaccination downregulated the expression of the cytokines.

[Example 2] Assay of Inhibitory Potential of Attenuated *Streptococcus pneumoniae* Strain THpep27 Against Allergic Disease 1. Materials and Methods 1.1. Attenuated *Streptococcus pneumoniae* Strain THpep27

The Δpep27 *Streptococcus pneumoniae* strain (THpep27, D39Δpep27::Cheshire) is the strain reported by Choi S Y et al. (Inactivated pep27 mutant as an effective mucosal vaccine against a secondary lethal pneumococcal challenge in mice. Clin Exp Vaccine Res. 2013), which is the same as the pep27-mutated *Streptococcus pneumoniae* disclosed in Korean Patent No. 10-1252911, with the exception that erythromycin resistant marker (ermAM) for selection is not comprised.

A Cheshire cassette (GenBank accession No. FJ981645) carrying the erythromycin-resistance marker (ermAM), which can be used as a temporary marker for selection, was amplified using primers (5'-TGG CTT ACC GTT CGT ATA G-3' (SEQ ID NO: 2) and 5'-TCG ATA CCG TTC GTA TAA TGT-3' (SEQ ID NO: 3)), which were granted by Dr. Donald Morrison (University of Illinois at Chicago), and ligated by polymerase chain reaction (PCR), with upstream and downstream sequences amplified with primers (5'-TCT CTA TCG GCC TCA AGC AG-3' (SEQ ID NO: 4) and 5'-CTA TAC GAA CGG TAA GCC A GAT TTT CAC CAC TGC TTT CG-3' (SEQ ID NO: 5), and 5'-ACA TTA TAC GAA CGG TAT CGA AAG GCC AGC AAG AGA CTA-3' (SEQ ID NO: 6) and 5'-CTG CGA GGC TTG CAC TGT AG-3' (SEQ ID NO: 7) from the genomic DNA of D39, which served as a template. Subsequently, the ligated product was then transformed into D39 to create a pep27 mutant.

Cheshire cassette excision was induced by adding 1% L-fucose (Sigma, St. Louis, Mo., USA). The fucose-treated cultures were then spread on THY blood agar plates to form a single colony. The presence of the Cheshire cassettes in each colony was confirmed by PCR using the following primers: 5'-TCT CTA TCG GCC TCA AGC AG-3' (SEQ ID NO: 8) and 5'-CTG CGA GGC TTG CAC TGT AG-3' (SEQ ID NO: 9). The mutant (THpep27) sequence was confirmed by nucleotide sequencing (Cosmo, Seoul, Korea) as well as by immunoblot analysis with Pep27 antibody (data not shown).

To confirm the THpep27 mutant at the RNA level, RNA was isolated from bacteria in the early exponential phase by using the conventional hot phenol method. After removal of DNA by DNase I (Takara, Tokyo, Japan), one microgram of bacterial RNA was reverse-transcribed into cDNA by using random primers (Takara). Reverse transcription PCR was performed by using the primers according to the manufacturer's instructions (Super Bio, American Building Restoration Products Inc., Franklin, Wis., USA).

The THpep27 mutant *Streptococcus pneumoniae* strain thus formed was cultured in THY broth (0.5% yeast extract-supplemented Todd-Hewitt broth; Difco Laboratories) at 37° C. until $OD_{550}$ reached 0.3 ($1 \times 10^8$ CFU/ml). The harvested bacterial culture was washed with PBS and then diluted in filtered PBS to a final concentration of $1 \times 10^8$ CFU/50 μl for use in immunization.

1.2. Experimental Animals

BALB/c female mice (five weeks old, Orient, Korea) were purchased and then acclimated for 7 days in an animal chamber before use. A mixture of 4:1 of ketamine (ketamine injection, Yuhan Corporation, Korea) and xylazine (Rompun, Bayer Korea Ltd.) was 2-fold diluted in PBS. Mice were anesthetized by intraperitoneal injection of 100 μl of the dilution thereinto. The anesthetization was followed by challenge and vaccination, and experiments using animals were conducted in accordance with the guidelines of Sungkyunkwan University Animal Ethical Committee.

1.3. Assay of Preventive Effect of Pep27 Mutant on Asthma

1) Mice were divided into three groups (n=7/group): a normal group fed with sterile water (PBS); a group in which asthma was induced with OVA (ovalbumin), followed by feeding sterile water thereto; and a group in which vaccination with pep27 mutant (Δpep27) was followed by asthma induction.

Figure 25:
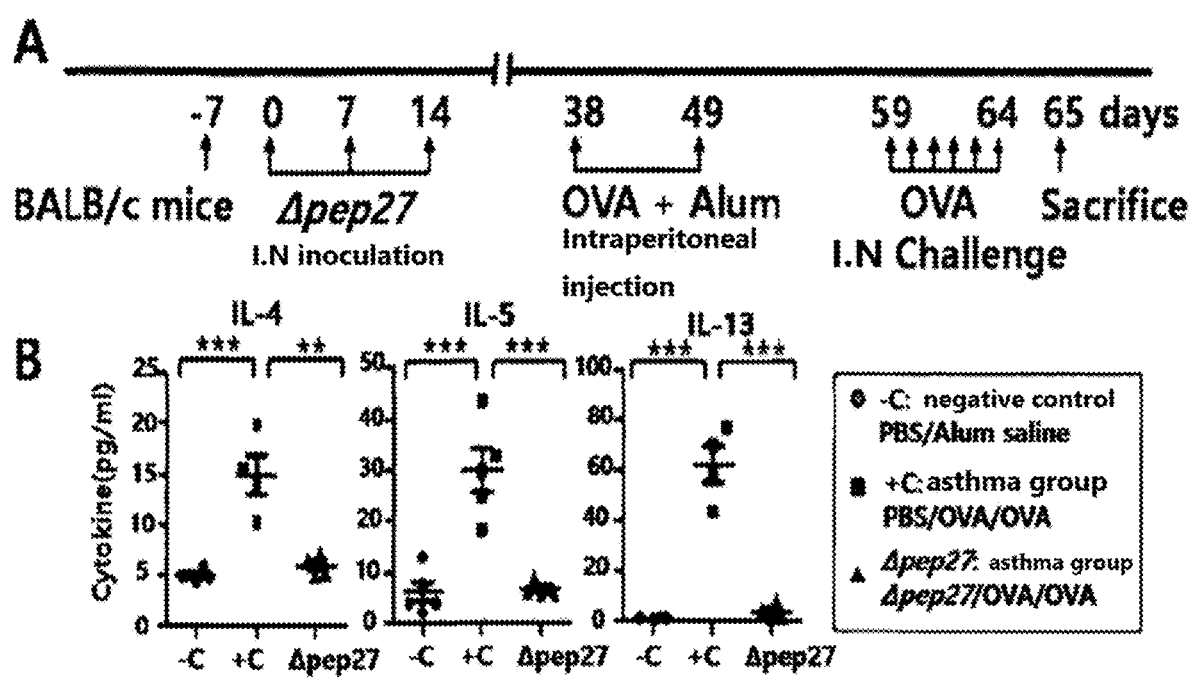
FIG. 25 illustrates a time schedule for a test for the preventive effect of Δpep27 mutant strain on allergic disease (A) and test data accounting for inhibitory effects of Δpep27 mutant strain on secretion of various allergic cytokines (B) in accordance with one embodiment of the present disclosure.
Figure 26:
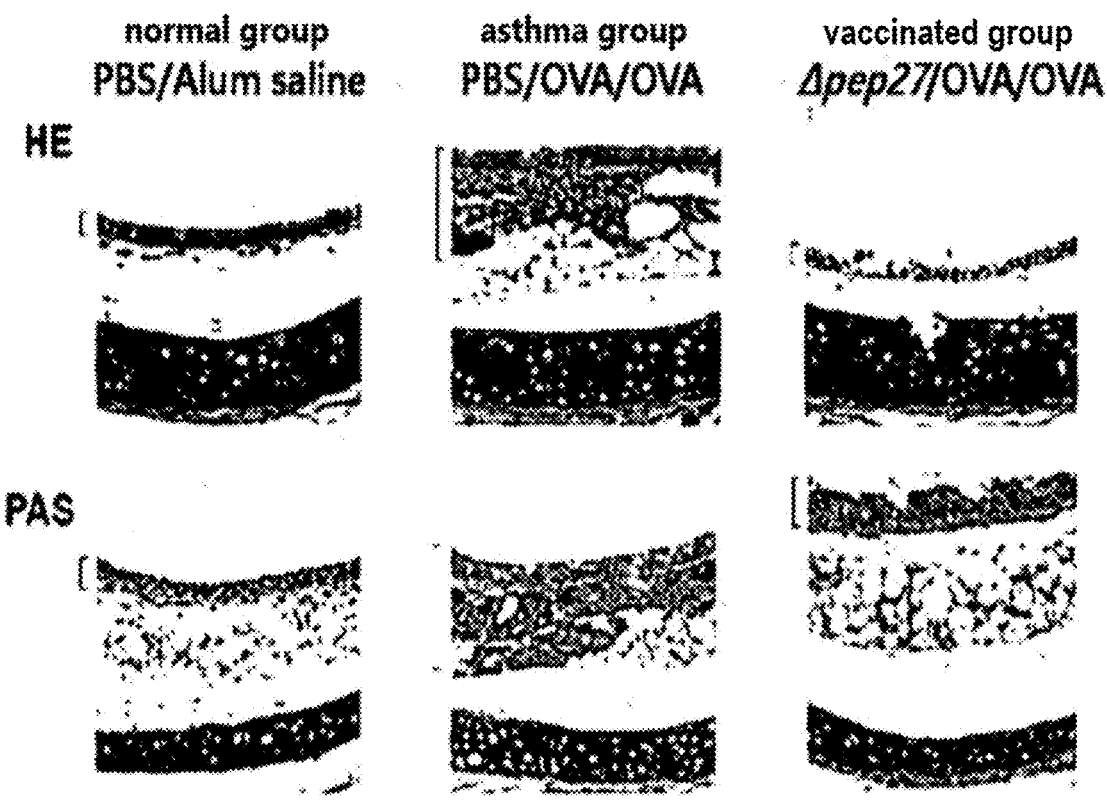
FIG. 26 shows histochemical staining results accounting for the preventive effect of Δpep27 mutant strain on allergic disease in accordance with one embodiment of the present disclosure.

2) On days 0, 7, and 14 after the start of the experiment, mice were anesthetized and intranasally (I.N) vaccinated with Δpep27 at $1 \times 10^8$ CFU/50 μl. On days 38 and 49 after starting of the experiment, the mice were sensitized by intraperitoneal injection of 100 μl of a sensitization solution which was prepared by voltexing 50 μg of OVA (Albumin from chicken egg white, Sigma Chemical Co., USA) and 2 mg of Alum (Aluminum hydroxide hydrate, Thermo Co., USA) in 100 μl of 0.9% saline (pH 4.0, Dyne Bio Inc., Korea) for 4 hours at 4° C. Subsequently, the mice were each challenged with 25 μl of a 0.4 mg/ml solution of OVA in biological saline every day for six days from day 59 to day 64 by dropwise adding 12.5 μl of the solution to each of the both intranasal regions (finally administered in a total amount of OVA 10 μg/mouse) to induce asthma. Twenty four hours after the last OVA challenge, the experimental animals were sacrificed and bronchoalveolar lavage fluid (BALF) was collected therefrom and measured for levels of cytokines. Lung tissues were excised, fixed, and stained with hematoxylin-eosin (H&E) (FIGS. 25 and 26).

1.4. Assay for Therapeutic Effect on Asthma

1) Mice were divided into three groups (n=7/group): a normal group fed with sterile water (PBS); a group in which asthma was induced with OVA (ovalbumin) (asthma-induced group); and a group in which asthma was induced with OVA, followed by vaccination with pep27 mutant strain (Δpep27) (asthma-cured experimental group).

Figure 27:
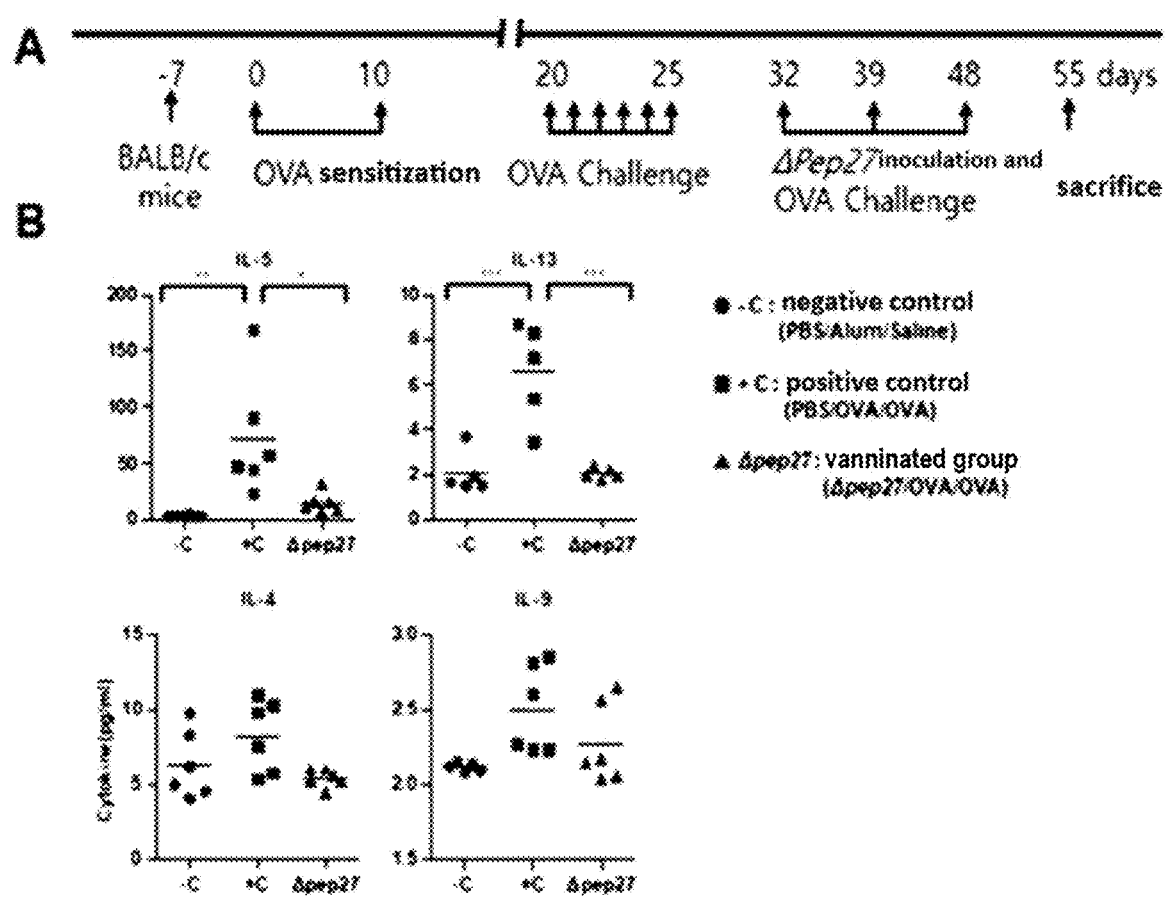
FIG. 27 illustrates a time schedule for a test for the therapeutic effect of Δpep27 mutant strain on allergic disease (A) and test data accounting for inhibitory effects of Δpep27 mutant strain on secretion of various allergic cytokines (B) in accordance with one embodiment of the present disclosure.

2) Asthma-induced group: Briefly, all the groups exclusive of the normal group were sensitized on days 0 and 10 after starting of the experiment by intraperitoneally injecting 100 μl of a sensitization solution, which was prepared by voltexing 50 μg of OVA (albumin from chicken egg white, Sigma Chemical Co., USA) and 2 mg of Alum (Aluminum hydroxide hydrate, Thermo Co., USA) in 100 μl of 0.9% saline (pH 4.0, Dyne Bio Inc., Korea) for 4 hours at 4° C. Ten days later, the mice were each challenged with 25 μl of a 0.4 mg/ml solution of OVA in biological saline every day for six days from day 20 to day 25 by administration of 12.5 μl of the solution to each of the both intranasal regions (in a total amount of OVA 10 μg/mouse). For the normal group, biological saline was provided alone (FIG. 27A).

3) Asthma therapy experiment group: One week after the same OVA challenge as in 2), the mice were immunized by intranasally immunizing Δpep27 at $1 \times 10^8$ CFU/50 μl once per week for a total of three times. Over three weeks of treatment, the mice were I.N challenged with OVA at a dose of 10 μg/25 μl from three days before vaccine administration three times a week (9 times in total) so as to induce asthma. One week after the last vaccination, the mice were finally challenged with OVA, 24 hours after which the mice were sacrificed (FIG. 27B).

1.5. Histochemical Analysis

Figure 28:
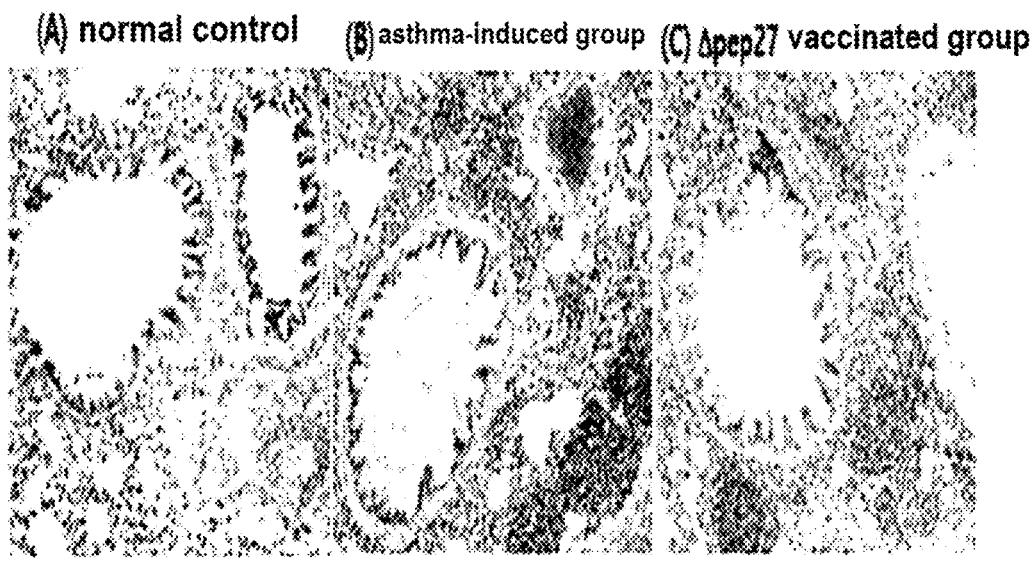
FIG. 28 shows histochemical staining results accounting for the therapeutic effect of Δpep27 mutant strain on allergic disease in accordance with one embodiment of the present disclosure.

Pulmonary and bronchial tissues were isolated and fixed with 10% (v/v) formaldehyde, followed by paraffin blocking. The paraffin-blocked tissues were cut into sections 4 μm thick before H&E staining. The H&E stained tissues were photographed using an optical microscope. Histochemical analysis was entrusted to KNOTUS Co., Ltd. (Korea) (FIG. 28).

1.6. Cytokine Analysis

Bronchoalveolar lavage fluid (BALF) was collected and measured for cytokine levels. In brief, the trachea of mouse was exposed and a catheter was inserted into the trachea. Through the catheter, 1.0 ml of PBS for BAL was slowly instilled into the bronchioles, and about 0.9 ml was aspirated. This fluid was loaded as it was, followed by recovering lavage fluid. The procedure was repeated twice more to obtain BALF in a total of 0.8 ml. The BALF obtained was centrifuged at 3,000 rpm for 10 min at 4° C. Then, the supernatant was separated as BALF for measuring cytokine levels and stored at −70° C. in a deep freezer until use. Cytokine levels in BALF were measured using an ELISA kit (ELISA Ready-SET-Go!, eBioscience, San Diego).

1.7. Statistics

Experimental data was expressed as mean±standard deviation. Statistical processing for cytokine measurements was performed with One-Way ANOVA. Statistical comparison of each group was conducted by Bonferroni's test (*, $P \leq 0.05$; , $P \leq 0.01$; *, $P \leq 0.001$). All P-values <0.05 were considered significant.

2. Result

2.1. Preventive Efficacy of Pep27 Mutant (ΔPep27) Against Asthma

2.1.1. Inhibition of Asthma-Induced Cytokine Secretion by ΔPep27 Vaccination When cytokine levels in the alveoli were measured using an ELISA kit, respective levels of allergy inducing cytokines IL-4, IL-5, and IL-13(Th2 cytokine; Cho et al., 2002) in the Δpep27-vaccinated group were remarkably reduced, compared to the asthma group and were as low as those in the normal group (FIG. 25).

2.1.2. Suppression of Airway Edema in Asthma by ΔPep27 Vaccination

In airway allergy diseases, allergens induce inflammation, making the airway remarkably thick (FIG. 26, asthma group). After immunohistochemical staining of inflammatory cells (hematoxylin-eosin, HE) and goblet cells (Periodic acid Schiff, PAS), the cells were observed at 400 magnifications to have remarkably reduced inflammation in Δpep27-vaccinated group, compared to the asthma group, with a similar level to that of the control (FIG. 26, vaccinated group).

2.2. Therapeutic Efficacy of Pep27 Mutant (ΔPep27) for Asthma

2.2.1. Therapeutic Efficacy of ΔPep27 Vaccine by Suppressing Asthma-Related Cytokines Mice were immunized with the Δpep27 vaccine once a week for a total of three times and one week after the last immunization, levels of cytokines in BALF from the mice were quantitated (FIG. 27A). Levels of Th2 cytokines (IL-4, IL-5, IL-13) were remarkably increased in the asthma group, but were similar between the vaccinated group and the normal group (FIG. 27B).

2.2.2. Therapeutic Efficacy of ΔPep27 Vaccine by Suppressing Pulmonary Inflammation After completion of the experiment, lungs of the mice were stained with hematoxylin-eosin (HE). The Δpep27-vaccinated group (C) was observed to have remarkably suppressed inflammation, compared to the asthma-induced group (B). Particularly, the vaccinated group exhibited almost the same morphology as in the normal control (A) as infiltration and mucosal secretion of inflammation cells around bronchus and blood vessels were suppressed (FIG. 28).

3. Discussion

It is disclosed in articles so far reported for prevention/treatment of asthma by using microorganisms that inhalation of inactivated *Mycobacterium phlei* suppresses bronchial hypersensitivity in children with moderate asthma (Ming et al., 2013) and inhibits IL-23R expression to regulate IL-17-producing γδT cell-mediated airway inflammation, thus relieving asthma (Ming et al., 2017). In addition, it is reported that intranasal immunization with the attenuated pertussis strain BPZE1 in mice reduced allergic airway inflammation and contact skin hyper responsiveness and thus can be used for preventing and treating such diseases (Li et al., 2012). As reported, immunization with diphtheria or attenuated tetanus toxin alone or in combination with pertussis whole cell vaccine suppress Th2 immune responses induced by allergen in mouse models and thus can be used for inhibiting airway inflammation or hyper-responsiveness (Gruber et al., 2006).

Also, infection with *Streptococcus pneumoniae* induces regulatory T cells, thus suppressing allergic airway diseases (Preston et al., 2011). Furthermore, intranasal immunization with currently marketed *Streptococcus pneumoniae* conjugate vaccines inhibits progression into airway allergic disease, but no effects were obtained upon intramuscular injection (Thorburn et al., 2010). It was thus revealed that injection of the polysaccharides and attenuated toxin of *Streptococcus pneumoniae* into airway suppresses allergic airway disease and induces regulatory T cells, which inhibits the onset of allergic airway diseases, with the resultant avoidance and suppression of immune responses to allergens (Thorburn et al., 2013). However, because all bacteria used in preventing and treating asthma are very toxic, except for attenuated *Bordetella pertussis*, inactivated bacteria or particular components must be employed. In addition, intranasal immunization is reported to exhibit a higher inhibitory effect on airway allergic responses than subcutaneous immunization (Takabayashi et al., 2003).

Infection with *Bordetella pertussis* induces Th1 responses (IFN-γ upregulation) in mouse allergic airway disease models, which may aggravate inflammation (Ennis et al., 2004; Cho et al., 2002; Kumar et al., 2004). Hence, it is necessary to suppress allergic responses without upregulating IFN-γ expression. When instillation of killed *Streptococcus pneumoniae* into airway was measured for asthma preventing effects, Th1 responses were induced without significant suppression of IL-5 and IL-13 levels, so that IFN-γ expression was significantly upregulated (Preston et al., 2007; Gibson et al., 2012; U.S. Pat. No. 8,226,959). That is, despite suppression of Th2 responses, the induction of Th1 responses cannot exclude the possibility of aggravating inflammation. Thus, Gibson et al. (2012; U.S. Pat. No. 8,226,959) focused on separated *Streptococcus pneumoniae* components that have inhibitory effects on allergic airway diseases.

When used, however, the attenuated pep27 mutant (Δpep27) of the present disclosure significantly suppressed the expression of Th2 cytokines (IL-13 and IL-4) as well as Th1 cytokine (IFN-γ) to normal levels, with similarity to the normal group in terms of histological opinions. Therefore, a pharmaceutical composition comprising the attenuated *Streptococcus pneumoniae* strain according to the present disclosure is expected to be a safer agent for prevention or treatment of allergic diseases, compared to conventional vaccines or medicines.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

It is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A pharmaceutical composition for preventing or treating an inflammatory disease, an infectious disease caused by a respiratory virus, an infectious disease caused by a bacterium other than *Streptococcus pneumoniae*, or an allergic disease, the composition comprising an attenuated *Streptococcus pneumoniae* strain, wherein the attenuated *Streptococcus pneumoniae* strain comprises a mutant pep27 gene in which the nucleotide residues at positions 1 to 53 on the pep27 nucleotide sequence represented by SEQ ID NO: 1 are deleted, and wherein the allergic disease is an allergic respiratory disease selected from the group consisting of asthma, allergic rhinitis, sinusitis, and chronic obstructive pulmonary disease.

2. The pharmaceutical composition of claim 1, wherein the inflammatory disease is selected from the group consisting of asthma, bronchitis, pneumonia, sepsis, rhinitis, inflammatory bowel diseases, gastroenteritis, colitis, Crohn's disease, pancreatitis, atherosclerosis, and arthritis.

3. The pharmaceutical composition of claim 1, wherein the respiratory virus is selected from the group consisting of metapneumovirus, coronavirus, enterovirus, respiratory syncytial virus, adenovirus, bocavirus, rhinovirus, and influenza virus.

4. The pharmaceutical composition of claim 1, wherein the infectious disease is caused by a Gram-positive bacterium or a Gram-negative bacterium.

5. The pharmaceutical composition of claim 4, wherein the Gram-positive bacterium is selected from the group consisting of *Staphylococcus, Streptococcus, Clostridium tetani,* and *Bacillus anthracis,* and the Gram-negative bacterium is selected from the group consisting of *Salmonella, Shigella, Klepsiella pneumoniae, E. coli,* and *Vibrio cholerae.*

6. The pharmaceutical composition of claim 1, wherein the allergic disease is selected from the group consisting of hives, allergic conjunctivitis, pollen allergy, atopy, food allergy, allergic tympanitis, anaphylactic shock, contact hypersensitivity, allergic contact dermatitis, bacterial allergy, fungal allergy, viral allergy, drug allergy, and allergic encephalitis.

7. The pharmaceutical composition of claim 1, wherein the composition is capable of immunization in a serotype-independent manner.

8. The pharmaceutical composition of claim 1, wherein the attenuated *Streptococcus pneumoniae* strain suppresses production of a Th1 cytokine and a Th2 cytokine.

9. The pharmaceutical composition of claim 8, wherein the Th1 cytokine is selected from the group consisting of interferon-gamma (IFN-γ), tumor necrosis factor alpha (TNF-α), and interleukin-12 (IL-12), and the Th2 cytokine is selected from the group consisting of interleukin-4 (IL-4), interleukin-5 (IL-5), and interleukin-13 (IL-13).

10. The pharmaceutical composition of claim 1, wherein the composition is capable of being non-invasive to a lung, a spleen, blood, or a brain.

11. The pharmaceutical composition of claim 1, being configured to be administered via an intraperitoneal, an intranasal route, or intramucosal route.

12. The pharmaceutical composition of claim 1, further comprising a pharmaceutically acceptable carrier or an adjuvant.

* * * * *

```
                        SEQUENCE LISTING

<160> NUMBER OF SEQ ID NOS: 17

<210> SEQ ID NO 1
<211> LENGTH: 84
<212> TYPE: DNA
<213> ORGANISM: Artificial Sequence
<220> FEATURE:
<223> OTHER INFORMATION: synthesized

<400> SEQUENCE: 1
atgagaaagg aatttcacaa cgttttatct agtgatcagt tacttacaga caaaaggcca         60
gcaagagact ataatagaaa atag                                                84

<210> SEQ ID NO 2
<211> LENGTH: 19
<212> TYPE: DNA
<213> ORGANISM: Artificial Sequence
<220> FEATURE:
<223> OTHER INFORMATION: synthesized

<400> SEQUENCE: 2
tggcttaccg ttcgtatag                                                      19

<210> SEQ ID NO 3
<211> LENGTH: 21
<212> TYPE: DNA
<213> ORGANISM: Artificial Sequence
<220> FEATURE:
<223> OTHER INFORMATION: synthesized

<400> SEQUENCE: 3
tcgataccgt tcgtataatg t                                                   21

<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
tctctatcgg cctcaagcag                                                     20

<210> SEQ ID NO 5
<211> LENGTH: 39
<212> TYPE: DNA
<213> ORGANISM: Artificial Sequence
<220> FEATURE:
<223> OTHER INFORMATION: synthesized

<400> SEQUENCE: 5
ctatacgaac ggtaagccag attttcacca ctgctttcg                                39
```

```
<210> SEQ ID NO 6
<211> LENGTH: 39
<212> TYPE: DNA
<213> ORGANISM: Artificial Sequence
<220> FEATURE:
<223> OTHER INFORMATION: synthesized

<400> SEQUENCE: 6
acattatacg aacggtatcg aaaggccagc aagagacta                              39

<210> SEQ ID NO 7
<211> LENGTH: 20
<212> TYPE: DNA
<213> ORGANISM: Artificial Sequence
<220> FEATURE:
<223> OTHER INFORMATION: synthesized

<400> SEQUENCE: 7
ctgcgaggct tgcactgtag                                                   20

<210> SEQ ID NO 8
<211> LENGTH: 20
<212> TYPE: DNA
<213> ORGANISM: Artificial Sequence
<220> FEATURE:
<223> OTHER INFORMATION: synthesized

<400> SEQUENCE: 8
tctctatcgg cctcaagcag                                                   20

<210> SEQ ID NO 9
<211> LENGTH: 20
<212> TYPE: DNA
<213> ORGANISM: Artificial Sequence
<220> FEATURE:
<223> OTHER INFORMATION: synthesized

<400> SEQUENCE: 9
ctgcgaggct tgcactgtag                                                   20

<210> SEQ ID NO 10
<211> LENGTH: 19
<212> TYPE: DNA
<213> ORGANISM: Artificial Sequence
<220> FEATURE:
<223> OTHER INFORMATION: synthesized

<400> SEQUENCE: 10
agccacctca tgctagagc                                                    19

<210> SEQ ID NO 11
<211> LENGTH: 20
<212> TYPE: DNA
<213> ORGANISM: Artificial Sequence
<220> FEATURE:
<223> OTHER INFORMATION: synthesized

<400> SEQUENCE: 11
gcctggtctg gcatcactac                                                   20

<210> SEQ ID NO 12
<211> LENGTH: 20
<212> TYPE: DNA
<213> ORGANISM: Artificial Sequence
<220> FEATURE:
<223> OTHER INFORMATION: synthesized
```

```
<400> SEQUENCE: 12
ctggtgtgtg acgttcccat                                                    20

<210> SEQ ID NO 13
<211> LENGTH: 20
<212> TYPE: DNA
<213> ORGANISM: Artificial Sequence
<220> FEATURE:
<223> OTHER INFORMATION: synthesized

<400> SEQUENCE: 13
tgtcgttgct tggttctcct                                                    20

<210> SEQ ID NO 14
<211> LENGTH: 21
<212> TYPE: DNA
<213> ORGANISM: Artificial Sequence
<220> FEATURE:
<223> OTHER INFORMATION: synthesized

<400> SEQUENCE: 14
cacaagatgc tgggacagtg a                                                  21

<210> SEQ ID NO 15
<211> LENGTH: 20
<212> TYPE: DNA
<213> ORGANISM: Artificial Sequence
<220> FEATURE:
<223> OTHER INFORMATION: synthesized

<400> SEQUENCE: 15
tccttgatgg tggtgcatga                                                    20

<210> SEQ ID NO 16
<211> LENGTH: 18
<212> TYPE: DNA
<213> ORGANISM: Artificial Sequence
<220> FEATURE:
<223> OTHER INFORMATION: synthesized

<400> SEQUENCE: 16
tgcatcctgc accaccaa                                                      18

<210> SEQ ID NO 17
<211> LENGTH: 20
<212> TYPE: DNA
<213> ORGANISM: Artificial Sequence
<220> FEATURE:
<223> OTHER INFORMATION: synthesized

<400> SEQUENCE: 17
tccacgatgc caaagttgtc                                                    20
```